US010712924B2

(12) United States Patent
Hay

(10) Patent No.: US 10,712,924 B2
(45) Date of Patent: Jul. 14, 2020

(54) NON-CONTACTING MONITOR FOR BRIDGES AND CIVIL STRUCTURES

(71) Applicant: RDI TECHNOLOGIES, INC., Knoxville, TN (US)

(72) Inventor: Jeffrey R. Hay, Louisville, KY (US)

(73) Assignee: RDI TECHNOLOGIES, INC., Knoxville, TN (US)

( * ) Notice: Subject to any disclaimer, the term of this patent is extended or adjusted under 35 U.S.C. 154(b) by 0 days.

(21) Appl. No.: 16/679,905

(22) Filed: Nov. 11, 2019

(65) Prior Publication Data

US 2020/0073545 A1 Mar. 5, 2020

Related U.S. Application Data

(63) Continuation of application No. 15/731,350, filed on May 31, 2017, now Pat. No. 10,521,098, which is a (Continued)

(51) Int. Cl.
*G06K 9/00* (2006.01)
*G06F 3/0484* (2013.01)
(Continued)

(52) U.S. Cl.
CPC ........ *G06F 3/04847* (2013.01); *A61B 5/0077* (2013.01); *A61B 5/01* (2013.01); *A61B 5/024* (2013.01); *A61B 5/0816* (2013.01); *A61B 5/165* (2013.01); *A61B 5/4815* (2013.01); *A61B 5/7435* (2013.01); *G01N 29/44* (2013.01); *G06F 16/7335* (2019.01); *G06K 9/00335* (2013.01); *G06K 9/00771* (2013.01);
(Continued)

(58) Field of Classification Search
USPC ...................................... 348/82, 84, 86, 143
See application file for complete search history.

(56) References Cited

U.S. PATENT DOCUMENTS 5,517,251 A 5/1996 Rector et al.
5,666,157 A 9/1997 Aviv
(Continued)

OTHER PUBLICATIONS

"A vision-based approach for the direct measurement of displacements in vibrating System", Mazen et al, (Year: 2003).*
(Continued)

*Primary Examiner* — Daquan Zhao
(74) *Attorney, Agent, or Firm* — Wyatt, Tarrant & Combs, LLP; Stephen C. Hall

(57) ABSTRACT

A system for monitoring the movement of objects, structures, models of structures, cables and the like provides for the acquisition of images with an optical sensing device such as a video camera fixedly mounted at a selected distance from the item studied, in which the images are arranged into frames divided into pixels which are characterized by an intensity reflected or emitted over a selected time interval, and a data processing system to calculate a physical displacement as function of time of the item being studied or a portion of the item being studied based on an output from the video camera, and in some embodiments the system visually distinguishes one or more locations in the frame to indicate a difference in the phase of motion for multiple objects appearing in the frame.

22 Claims, 14 Drawing Sheets

Related U.S. Application Data continuation of application No. 14/757,255, filed on Dec. 9, 2015, now Pat. No. 9,704,266.

(60) Provisional application No. 62/209,979, filed on Aug. 26, 2015, provisional application No. 62/161,228, filed on May 13, 2015, provisional application No. 62/154,011, filed on Apr. 28, 2015, provisional application No. 62/139,110, filed on Apr. 14, 2015, provisional application No. 62/146,744, filed on Apr. 13, 2015, provisional application No. 62/141,940, filed on Apr. 2, 2015, provisional application No. 62/139,127, filed on Mar. 27, 2015, provisional application No. 62/090,729, filed on Dec. 11, 2014.

(51) Int. Cl.

| | |
|---|---|
| G06F 16/732 | (2019.01) |
| A61B 5/00 | (2006.01) |
| A61B 5/01 | (2006.01) |
| A61B 5/024 | (2006.01) |
| A61B 5/08 | (2006.01) |
| A61B 5/16 | (2006.01) |
| G06T 7/00 | (2017.01) |
| G01N 29/44 | (2006.01) |
| G06T 7/11 | (2017.01) |
| G06T 7/246 | (2017.01) |
| G06T 7/262 | (2017.01) |
| H04N 7/18 | (2006.01) |

(52) U.S. Cl.
CPC .............. *G06T 7/0016* (2013.01); *G06T 7/11* (2017.01); *G06T 7/248* (2017.01); *G06T 7/262* (2017.01); *G01N 2291/028* (2013.01); *G06T 2200/24* (2013.01); *G06T 2207/10016* (2013.01); *G06T 2207/20056* (2013.01); *G06T 2207/20216* (2013.01); *G06T 2207/30004* (2013.01); *G06T 2207/30164* (2013.01); *H04N 7/18* (2013.01)

(56) References Cited

U.S. PATENT DOCUMENTS

| | | | |
|---|---|---|---|
| 6,028,626 | A | 2/2000 | Aviv |
| 6,295,383 | B1 | 9/2001 | Smitt et al. |
| 6,422,741 | B2 | 7/2002 | Murphy et al. |
| 6,727,725 | B2 | 4/2004 | Devaney et al. |
| 6,774,601 | B2 | 8/2004 | Schwartz et al. |
| 6,792,811 | B2 | 9/2004 | Argento et al. |
| 7,622,715 | B2 | 11/2009 | Ignatowicz |
| 7,672,369 | B2 | 3/2010 | Garakani et al. |
| 7,710,280 | B2 | 5/2010 | McLellan |
| 7,862,188 | B2 | 1/2011 | Luty et al. |
| 7,903,156 | B2 | 3/2011 | Nobori et al. |
| 8,119,986 | B1 | 2/2012 | Garvey, III et al. |
| 8,149,273 | B2 | 4/2012 | Liu et al. |
| 8,170,109 | B2 | 5/2012 | Gaude et al. |
| 8,242,445 | B1 | 8/2012 | Scanlon et al. |
| 8,351,571 | B2 | 1/2013 | Brinks et al. |
| 8,374,498 | B2 | 2/2013 | Pastore |
| 8,475,390 | B2 | 7/2013 | Heaton et al. |
| 8,483,456 | B2 | 7/2013 | Nagatsuka et al. |
| 8,502,821 | B2 | 8/2013 | Louise et al. |
| 8,515,711 | B2 | 8/2013 | Mitchell et al. |
| 8,526,674 | B2 | 9/2013 | Patti |
| 8,537,203 | B2 | 9/2013 | Seibel et al. |
| 8,693,735 | B2 | 4/2014 | Kielkopf et al. |
| 8,720,781 | B2 | 5/2014 | Wang et al. |
| 8,731,241 | B2 | 5/2014 | Johnson et al. |
| 8,765,121 | B2 | 7/2014 | Maslowski |
| 8,774,280 | B2 | 7/2014 | Tourapis et al. |
| 8,797,439 | B1 | 8/2014 | Coley et al. |
| 8,803,977 | B2 | 8/2014 | Uchima et al. |
| 8,811,708 | B2 | 8/2014 | Fischer et al. |
| 8,823,813 | B2 | 9/2014 | Mantzel et al. |
| 8,831,370 | B2 | 9/2014 | Archer |
| 8,874,374 | B2 | 10/2014 | Bogucki |
| 8,879,789 | B1 | 11/2014 | Figov et al. |
| 8,879,894 | B2 | 11/2014 | Neuman et al. |
| 8,884,741 | B2 | 11/2014 | Cavallaro et al. |
| 8,897,491 | B2 | 11/2014 | Ambrus et al. |
| 8,924,163 | B2 | 12/2014 | Hudson et al. |
| 9,006,617 | B2 | 4/2015 | Mullen |
| 9,075,136 | B1 | 7/2015 | Joao |
| 10,250,868 | B1 | 4/2019 | Arnold |
| 2002/0005895 | A1 | 1/2002 | Freeman |
| 2004/0032924 | A1 | 2/2004 | Judge, Jr. |
| 2004/0081369 | A1 | 4/2004 | Gindele et al. |
| 2004/0160336 | A1 | 8/2004 | Hock et al. |
| 2004/0184529 | A1 | 9/2004 | Henocq et al. |
| 2004/0196448 | A1 | 10/2004 | Rembe |
| 2006/0009700 | A1 | 1/2006 | Brumfield et al. |
| 2006/0049707 | A1 | 3/2006 | Vuyyuru |
| 2007/0061043 | A1 | 3/2007 | Ermakov et al. |
| 2007/0276270 | A1 | 11/2007 | Tran |
| 2009/0010570 | A1 | 1/2009 | Yamada et al. |
| 2009/0083814 | A1 | 3/2009 | Sekine |
| 2009/0244261 | A1 | 10/2009 | Maehner |
| 2009/0273704 | A1 | 11/2009 | Picenti |
| 2010/0033579 | A1 | 2/2010 | Yokohata et al. |
| 2010/0042000 | A1 | 2/2010 | Schuhrke et al. |
| 2010/0091181 | A1 | 4/2010 | Capps |
| 2010/0328352 | A1 | 12/2010 | Shamir et al. |
| 2011/0019027 | A1 | 1/2011 | Fujita et al. |
| 2011/0152729 | A1 | 6/2011 | Oohashi et al. |
| 2012/0207218 | A1 | 8/2012 | Asamura et al. |
| 2013/0060571 | A1 | 3/2013 | Soemo et al. |
| 2013/0176424 | A1 | 7/2013 | Weil |
| 2013/0201316 | A1 | 8/2013 | Binder et al. |
| 2013/0342691 | A1 | 12/2013 | Lewis et al. |
| 2014/0002667 | A1 | 1/2014 | Cheben et al. |
| 2014/0072190 | A1 | 3/2014 | Wu et al. |
| 2014/0072228 | A1 | 3/2014 | Rubinstein et al. |
| 2014/0072229 | A1 | 3/2014 | Wadhwa et al. |
| 2014/0112537 | A1 | 4/2014 | Frank et al. |
| 2014/0169763 | A1 | 6/2014 | Nayak et al. |
| 2014/0205175 | A1 | 7/2014 | Tanaka et al. |
| 2014/0236036 | A1 | 8/2014 | de Haan et al. |
| 2014/0341470 | A1 | 11/2014 | Lee et al. |
| 2015/0134545 | A1* | 5/2015 | Mann ..................... G06Q 10/20 705/305 |
| 2015/0221534 | A1 | 8/2015 | van der Meulen |
| 2015/0239686 | A1 | 8/2015 | Stone |
| 2016/0085840 | A1 | 3/2016 | Dixit |
| 2016/0217587 | A1 | 7/2016 | Hay |
| 2018/0194314 | A1 | 7/2018 | Da Costa |

OTHER PUBLICATIONS

Wadhwa et al., "Phase-based Video Motion Processing", also see YouTube https://www.youtube.com/watch?v=W7ZQ-FG7Nvw, SIGGRAPH 2013.

Wu et al., "Eulerian Video Magnification for Revealing Subtle Changes in the World", ACM Transactions on Graphics (TOG)—Proceedings of ACM SIGGRAPH 2012 TOG Homepag, evolume 31 Issue 4, Jul. 2012, Article No. 65.

Liu et al., "Motion magnification", ACM Transactions on Graphics (TOG)—Proceedings of ACM SIGGRAPH 2005 TOG Homepage, vol. 24 Issue 3, Jul. 2005.

Rubinstein et al. ("Revealing Invisible Changes in the world" (YouTube), YouTube https://www.youtube.com/watch?v=e9ASH8IBJ2U, 2012.

Rubinstein et al. ("Eulerian Video Magnification" (YouTube), YouTube https://www.youtube.com/watch?v=ONZcjs1Pjmk, 2012).

Hay, J.R. "High Dynamic Range Imaging for the Detection of Motion", pp. 18-141; dissertation University of Louisville (Kentucky); May 2011.

(56) References Cited

OTHER PUBLICATIONS

Mazen Wahbeh et al, "A vision-based approach for the direct measurement of displacements in vibrating systems", Smart Mater. Struct., Feb. 11, 2003, 12, 785-794, Institute of Physics Publishing, IOP Publishing Ltd., UK.

* cited by examiner

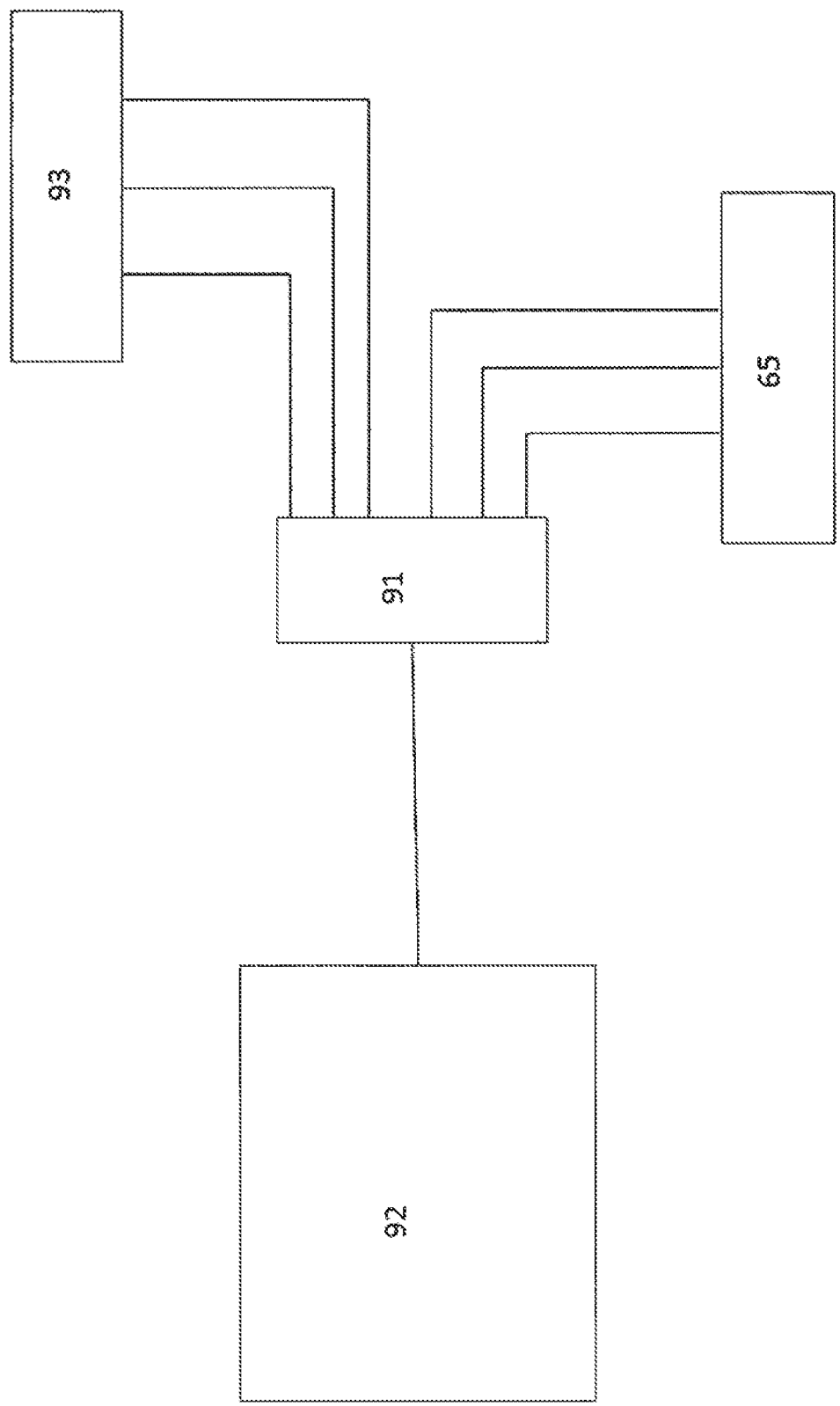

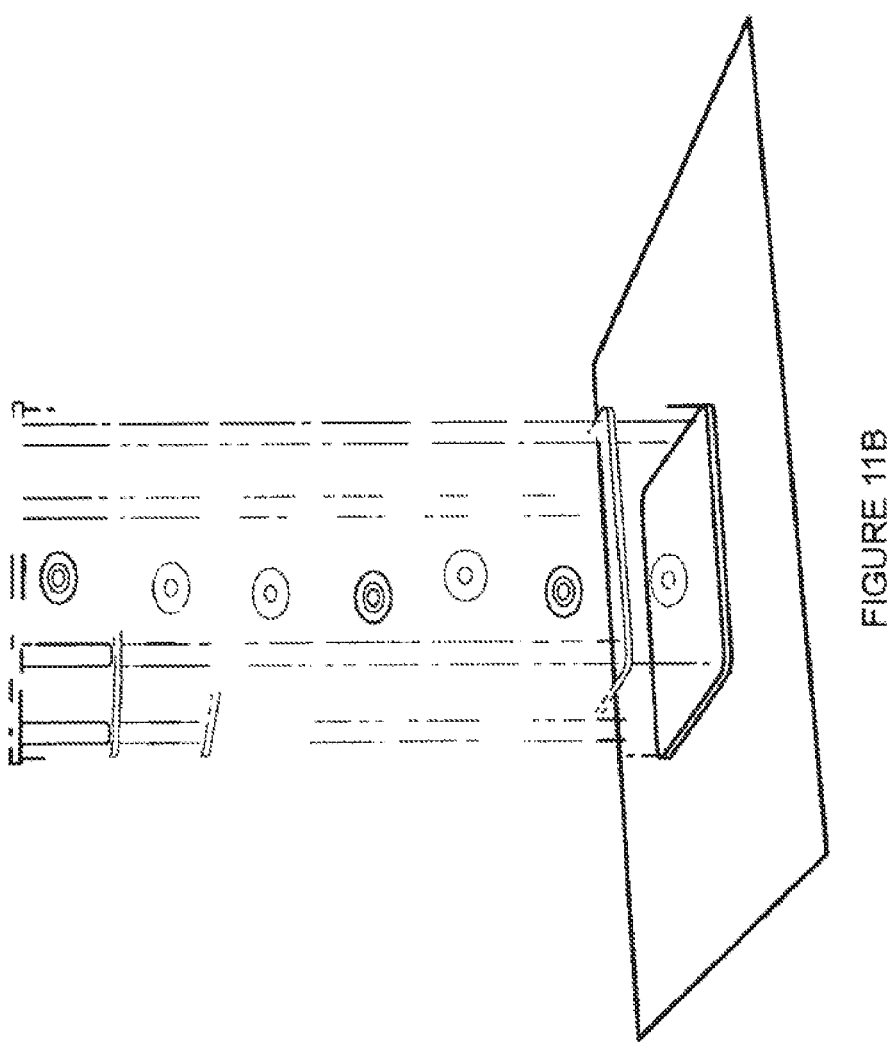

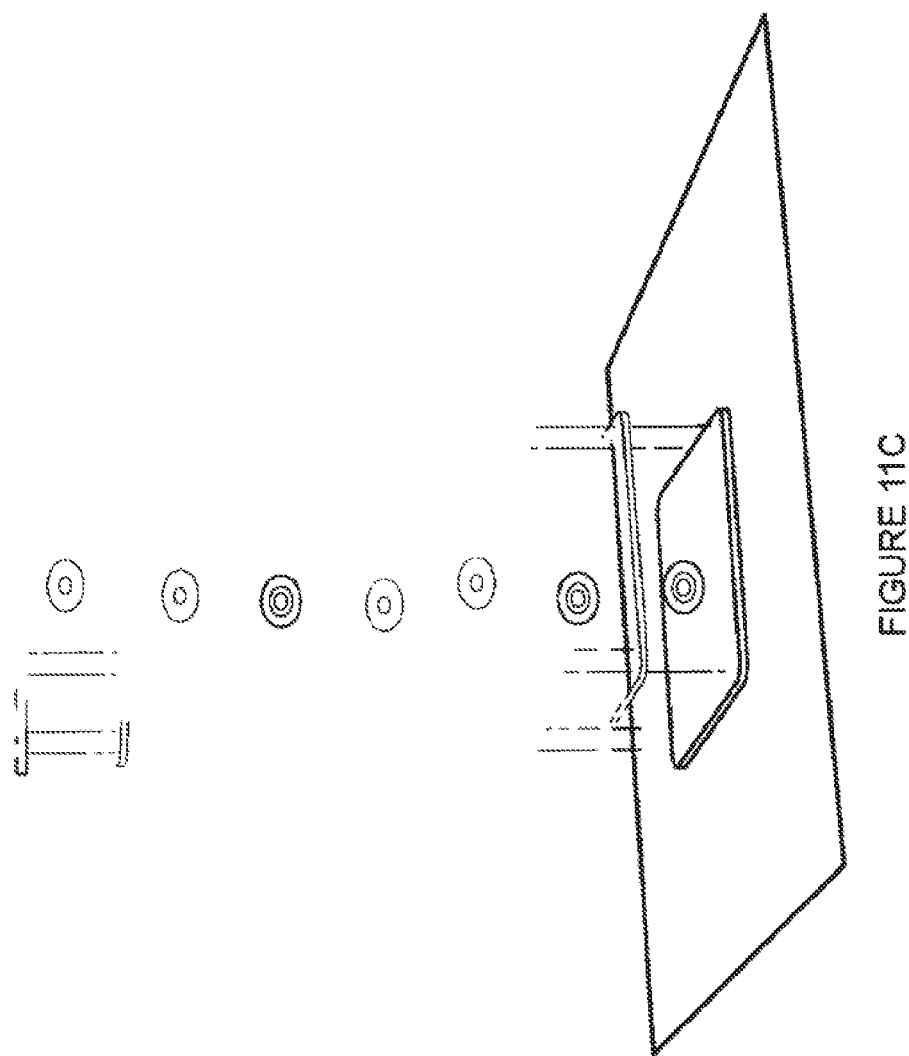

NON-CONTACTING MONITOR FOR BRIDGES AND CIVIL STRUCTURES

CROSS-REFERENCE TO RELATED APPLICATIONS

This continuation patent application claims the benefit of and priority to U.S. patent application Ser. No. 15/731,350, "Non-contacting monitor for bridges and civil structures", filed by the present inventor on May 31, 2017, which is a continuation of U.S. patent application Ser. No. 14/757,255, "Non-contacting monitor for bridges and civil structures", filed by the present inventor on Dec. 9, 2015, now U.S. Pat. No. 9,704,266, issued on Jul. 1, 2017, and incorporated herein by reference in its entirety. This continuation application claims the benefit of each of the following Provisional patent applications filed by the present inventor: Ser. No. 62/090,729, "Optical detection of periodic movement", filed on Dec. 11, 2014; Ser. No. 62/139,127, "Method for determining, comparing, measuring, and displaying phase", filed on Mar. 27, 2015; Ser. No. 62/141,940, "Method and system for analysis of structures and objects from spatio-temporal data", filed on Apr. 2, 2015; Ser. No. 62/139,110, "Adaptive array comparison", filed on Apr. 14, 2015; Ser. No. 62/146,744, "Method of analyzing, displaying, organizing, and responding to vital signals", filed on Apr. 13, 2015; Ser. No. 62/154,011, "Non contact optical baby monitor that senses respiration rate and respiratory waveform", filed on Apr. 28, 2015; Ser. No. 62/161,228, "Multiple region perimeter tracking and monitoring", filed on May 13, 2015; and Ser. No. 62/209,979, "Comparative analysis of time-varying and static imagery in a field", filed on Aug. 26, 2015, by the present inventors; the disclosures of each of which are incorporated herein by reference in their entirety.

This application is related to the following applications, filed on Dec. 9, 2015 by the present inventor: U.S. Ser. No. 14/757,256, "Method of analyzing, displaying, organizing, and responding to vital signals", U.S. Ser. No. 14/757,245, "Method of analyzing periodic motions in machinery", U.S. Ser. No. 14/757,259, "Method of adaptive array comparison for the detection and characterization of periodic motion" the entire disclosures of each and every one of which are incorporated herein by reference.

BACKGROUND OF THE INVENTION

Field of the Invention

The invention pertains to apparatus and methods for monitoring the movement of a structural member under a transient load. More specifically, the invention pertains to a non-contacting monitor for bridges, other civil structures, and models thereof.

Description of Related Art

There exists an overwhelming need for a cost efficient method of monitoring and assessing the health of our nation's infrastructure. Large-scale adoption of technology solutions in the infrastructure monitoring market would reduce the number of tragic and expensive failures, increase safety and public confidence in infrastructure, provide quantitative data for proper appropriation of funding for repairs, and streamline the inspection process facilitating state DOT compliance with federal bridge inspection regulations.

The current bridge health monitoring process is labor intensive, expensive, and largely empirical with little data available about real time bridge performance. All information that is currently compiled to determine a bridge rating is based on calculations derived from visual inspection, tools utilized to determine the quality of the materials in the bridge, and dye to look for cracks. None of these tools effectively rates the bridge on actual current performance under load because the only tools available for such measurements are expensive and not feasible for widespread use. Current infrastructure assessment techniques do not provide a safe environment for inspectors, as they require the use of bucket trucks, rappelling, and other risky means of getting the inspector close to the infrastructure to perform a thorough visual inspection. The inspector is also subject to danger from vehicular traffic around the inspection site.

There is a clear need for a low cost, simple to use, inspection technology to provide infrastructure inspection technicians with information that will solve several key problems with current inspection practices including: reducing the amount of time and money spent on inspections by providing data from areas that are difficult and time consuming to access, and quantifying inspections, which have traditionally been somewhat subjective visual inspections.

Objects and Advantages

Objects of the present invention include the following: providing a system for measuring the movement of a structural member in response to a transient load; providing a non-contacting monitor for bridges; providing a system for quantitatively evaluating the response of a structural member to dynamic loads to evaluate the condition of a bridge or other civil structure; providing a system for inspecting a bridge and tracking the condition of the bridge over time; providing a system for comparing the condition of a bridge with that of similar bridges in other locations; providing a system to evaluate the condition of bridges, track their condition over time and in comparison to one another so that improvements and inspection schedules may be prioritized; providing a system for tracking and enforcing compliance with bridge load limits and related vehicle permitting; and, providing a system for non-contacting measurement of deflection of model structures during seismic testing and simulation. These and other objects and advantages of the invention will become apparent from consideration of the following specification, read in conjunction with the drawings.

SUMMARY OF THE INVENTION

According to one aspect of the invention, a system for monitoring bridge loading comprises:

an optical sensing device fixedly mounted at a selected distance from a bridge and having an unobstructed view of a selected portion of the bridge structure;

a data processing system to analyze the output of the optical sensing device and calculate a physical displacement of the selected portion of the bridge structure as a function of time;

a triggering system to trigger an event and generate a time stamp whenever the data processing system detects that the physical displacement exceeds a preset threshold indicating an overload condition;

at least one digital imaging device fixedly mounted proximate to the bridge and positioned to record images of the vehicles on the bridge at selected times;

a synchronized communication means between the data processing system and the digital imaging device so that the images of the vehicles on the bridge may be acquired and time stamped, so that vehicle(s) causing the displacement event may be identified; and, a data storage system to archive the time stamped images and the physical displacement data for later retrieval.

According to another aspect of the invention, a method for monitoring bridge loading comprises:

fixedly positioning an optical sensing device at a selected distance from a bridge and having an unobstructed view of a selected portion of the bridge structure;

fixedly positioning at least one digital imaging device proximate to the bridge and positioned to record images of vehicles on the bridge;

providing a data processing system in communication with the optical sensing device and the digital imaging device, the data processing system analyzing the output of the optical sensing device and calculating the physical displacement of the selected portion of the bridge structure as a function of time;

calibrating the data processing system by passing a test vehicle of known weight over the bridge so that a threshold level of displacement may be defined;

triggering an event and generating a time stamp whenever the physical displacement exceeds the threshold level, and causing the digital imaging device to record and time stamp the images of the vehicle(s) so that the vehicle(s) causing the displacement event may be identified; and, archiving the time-stamped images and time stamped displacement data for later retrieval and analysis.

According to another aspect of the invention, a system for monitoring the condition of a bridge comprises:

a video camera stably positioned at a selected distance from a bridge and having an unobstructed view of a selected portion of the bridge structure; and, a data processing system to analyze the output of the video camera over a selected time interval and calculate a physical displacement of the selected portion of the bridge structure as a function of time, and further including:

a GUI that displays:

a fixed image frame from the video camera, corresponding to a particular user-selected time within the time interval;

an indicator, movable by the user to select a portion of the structure for analysis; and, a display of displacement versus time for the selected portion over the selected time interval, and optionally having therein a first movable cursor for the user to select the particular time within the time interval.

According to another aspect of the invention, a method for monitoring the condition of a bridge comprises:

stably positioning a video camera at a selected distance from a bridge and having an unobstructed view of a selected portion of the bridge structure;

collecting a video file of the structure over a selected total time interval;

using a data processing system to analyze the video and calculate a physical displacement of the selected portion of the bridge structure as a function of time, wherein the data processing system is controlled through a GUI having at least the following features:

a display of a single video frame corresponding to a user-selected time within the total time interval;

a movable indicator superimposed on the video frame to allow the user to select an area of the bridge structure for analysis; and, a display of displacement versus time for the Region of Interest over the total time interval, the display optionally having therein a first movable cursor to allow the user to select a particular time within the total time interval and cause the video display to display the particular frame corresponding to that particular time; and, optionally populating a searchable database with the video file and selected metadata associated with the video file.

According to another aspect of the invention, a system for seismic testing comprises:

a seismic simulator having a horizontal platform upon which a model structure to be tested is placed, with mechanical actuators to allow the horizontal platform to be moved in three dimensions at selected amplitudes and frequencies under the direction of a control system;

a video camera stably positioned at a selected distance from the structure and having an unobstructed view of a selected portion of the structure; and, a data processing system to analyze the output of the video camera over a selected time interval and calculate a physical displacement of the selected portion of the structure as a function of time, and further including:

a GUI that displays:

a fixed image frame from the video camera, corresponding to a particular user-selected time within the time interval;

a movable indicator superimposed on the video frame to allow the user to select a portion of the structure for analysis; and, a display of displacement versus time for the selected portion over the selected time interval, and optionally having therein a first movable cursor for the user to select the particular time within the time interval.

According to another aspect of the invention, a method for seismic testing comprises:

placing a model structure to be tested on a seismic simulator having a horizontal platform with mechanical actuators to allow the horizontal platform to be moved in three dimensions at selected amplitudes and frequencies under the direction of a control system;

stably positioning a video camera at a selected distance from the structure and having an unobstructed view of a selected portion of the structure;

collecting a video file of the structure over a selected total time interval while the platform is operating under the direction of the control system;

using a data processing system to analyze the video and calculate a physical displacement of the selected portion of the structure as a function of time, wherein the data processing system is controlled through a GUI having at least the following features:

a display of a single video frame corresponding to a user-selected time within the total time interval;

a movable indicator superimposed on the video frame to allow the user to select an area of the structure for analysis; and, a display of displacement versus time for the selected area over the total time interval, the display optionally having therein a first movable cursor to allow the user to select a particular time within the total time interval and cause the video display to display the particular frame corresponding to that particular time.

BRIEF DESCRIPTION OF THE DRAWINGS

The drawings accompanying and forming part of this specification are included to depict certain aspects of the invention. A clearer conception of the invention, and of the components and operation of systems provided with the invention, will become more readily apparent by referring to the exemplary, and therefore non-limiting embodiments illustrated in the drawing figures, wherein like numerals (if they occur in more than one view) designate the same elements. The features in the drawings are not necessarily drawn to scale.

FIG. 9 is a schematic diagram of a system for synchronizing an image acquisition system with the drive signals of a three-axis seismic simulator.

FIG. 10A shows a video frame of a bridge after a truck (not shown) has passed over it. FIG. 10B shows a single phase mask at 2.25 Hz, which is the fundamental frequency of the bridge. FIG. 10C shows the same phase mask but multiplied by the intensity of the movement at each pixel.

FIGS. 11A-C illustrate the analysis of a seismic model, in which FIG. 11A is a frame of video of a model under seismic test, FIG. 11B is an image representing vibrations at 4.63 Hz, and FIG. 11C is an image representing vibrations at 2.84 Hz.

DETAILED DESCRIPTION OF THE INVENTION

Figure 1:
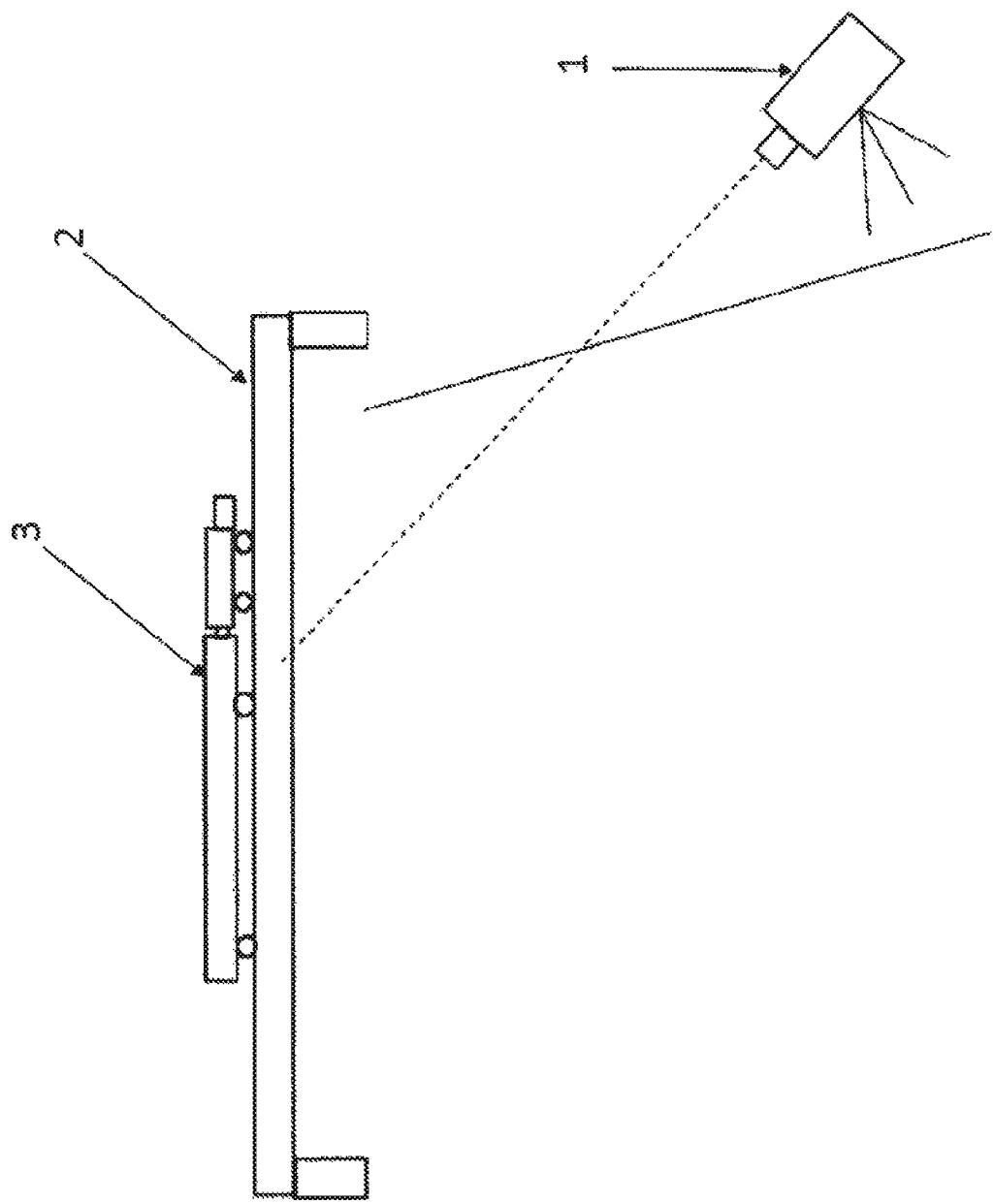
FIG. 1 is a schematic diagram of one embodiment of the present invention in which a camera is set up to acquire video images of a bridge.

In its most general sense, the invention comprises a non-contacting (optical) sensor positioned to observe a structural component that will be subject to dynamic loading. The optical sensor will, in many cases, preferably comprise a digital video camera capable of capturing a video file over a selected time interval. A system is provided to take the captured video (or other data file) and apply one or more analytical techniques to calculate the physical displacement or movement of a selected part of the structure. This is preferably done interactively by a user through an inventive graphical user interface (GUI) that allows the user to select a particular area of the component for detailed analysis, although it will be shown that some functions may be performed autonomously. A particularly novel and useful aspect of the system is that the user can select or change the area after the fact, i.e., from a single captured video file, the user is able to analyze the behavior of a first area over the entire time of the video file, then repeat the process for a second area, and so on. As will be shown in the Examples, this creates a unique ability to examine in detail the behavior of a large structure and evaluate possible points of weakness or deterioration using a single data file that can be collected quickly and safely. The analysis may involve calculating the maximum displacement, the frequency of any resonances that might be excited, the decay rate of vibrations, and the degree to which individual parts of the structure are moving in or out of phase with one another.

Various analytical or calculated data, and other identifying data, may be tagged as metadata associated with the video file and archived in a database for later retrieval. This feature allows the user to compare the performance of a particular structure over selected time intervals to monitor structural deterioration or aging, as well as to compare its performance to that of comparable structures to develop a statistical baseline, observe trends, prioritize maintenance and inspection strategies, and for other purposes. Among the metadata associated with the video file, there may be still images of the surrounding environment, e.g., traffic on a bridge, which may be time-stamped so that observed displacements may be correlated to vehicular loading for enforcement or other purposes.

The following Examples will serve to illustrate various aspects of the invention and how it may be used for various purposes. These Examples are intended for illustrative purposes only and are not intended to limit the scope of the invention as defined in the claims.

Bridge Analysis, Inspection, and Maintenance

In order to maintain the safety and integrity of transportation infrastructure, bridges are inspected at maintenance intervals defined by various standards and regulations. Such inspections are done by close visual inspection to look for cracks, corrosion, loose or missing bolts, and the like. It will be appreciated that this approach suffers from several shortcomings. First, it is time consuming and hazardous for the inspectors, requiring bucket trucks, rappelling, or other risky physical situations. Second, it is qualitative at best and doesn't provide a direct measure of the actual performance of the structure under loading. Third, because it isn't quantitative, the results are not easily compared to past results on the same structure or to the current performance of comparable structures elsewhere. Thus, trends are hard to spot and there is little opportunity to prioritize inspection and maintenance resources.

Example

FIG. 1 shows one setup for inspecting a bridge. A video camera 1 is placed stably on the ground, using a tripod or other suitable means, at some convenient distance from bridge 2 and having an unobstructed view of at least a portion of the bridge and preferably including a view of the traffic or vehicles 3 passing over the bridge deck. The video camera 1 collects a video file of sufficient length to include the passage of one or more selected vehicle(s) 3.

Example

Figure 2:
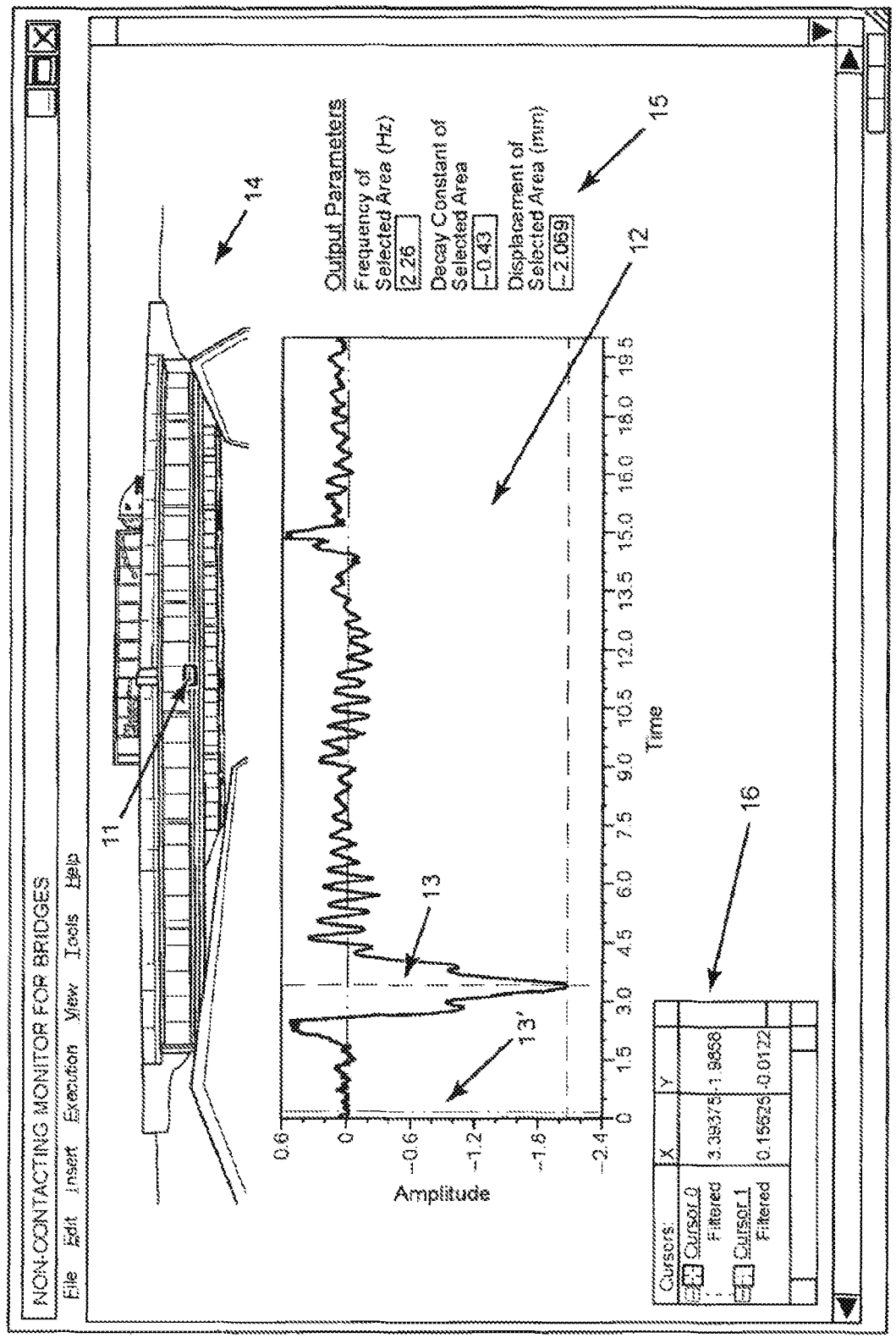
FIG. 2 is a schematic diagram of a GUI showing a plot of displacement of a selected area of the structure versus time over the length of the video file, a cursor indicating a user selected instant time, and a video frame corresponding to the selected instant time

FIG. 2 shows a screen shot of a graphical user interface (GUI) in accordance with one aspect of the invention. The screen displays a single image or frame 14 from the video file. To select a particular area of the structure for analysis the user can draw a box 11 in the image and the analysis for that location is automatically populated in the fields on the lower right. In this example, the output fields 15 include: Frequency of selected area (Hz), Decay constant of selected area, and Displacement of selected area (mm). An additional box 16 displays the location of cursors 13, 13'. The lower graph 12 shows the time waveform of displacement versus time over the course of the entire video acquisition for the area indicated by box 11 in the image. Graph 12 further includes cursors 13, 13' movable by the user along the time axis, to select a particular time interval. When the user moves cursor 13 the video frame 14 is updated so that it corresponds to that selected instant time. In this case, the user has selected the time corresponding to the maximum displacement of the selected area, and as can be seen from the video frame, this time correlates with the moment when the large truck 3 is directly over the area 11. The user can perform various analyses for the time interval defined by cursors 13, 13'.

Example

Figure 3:
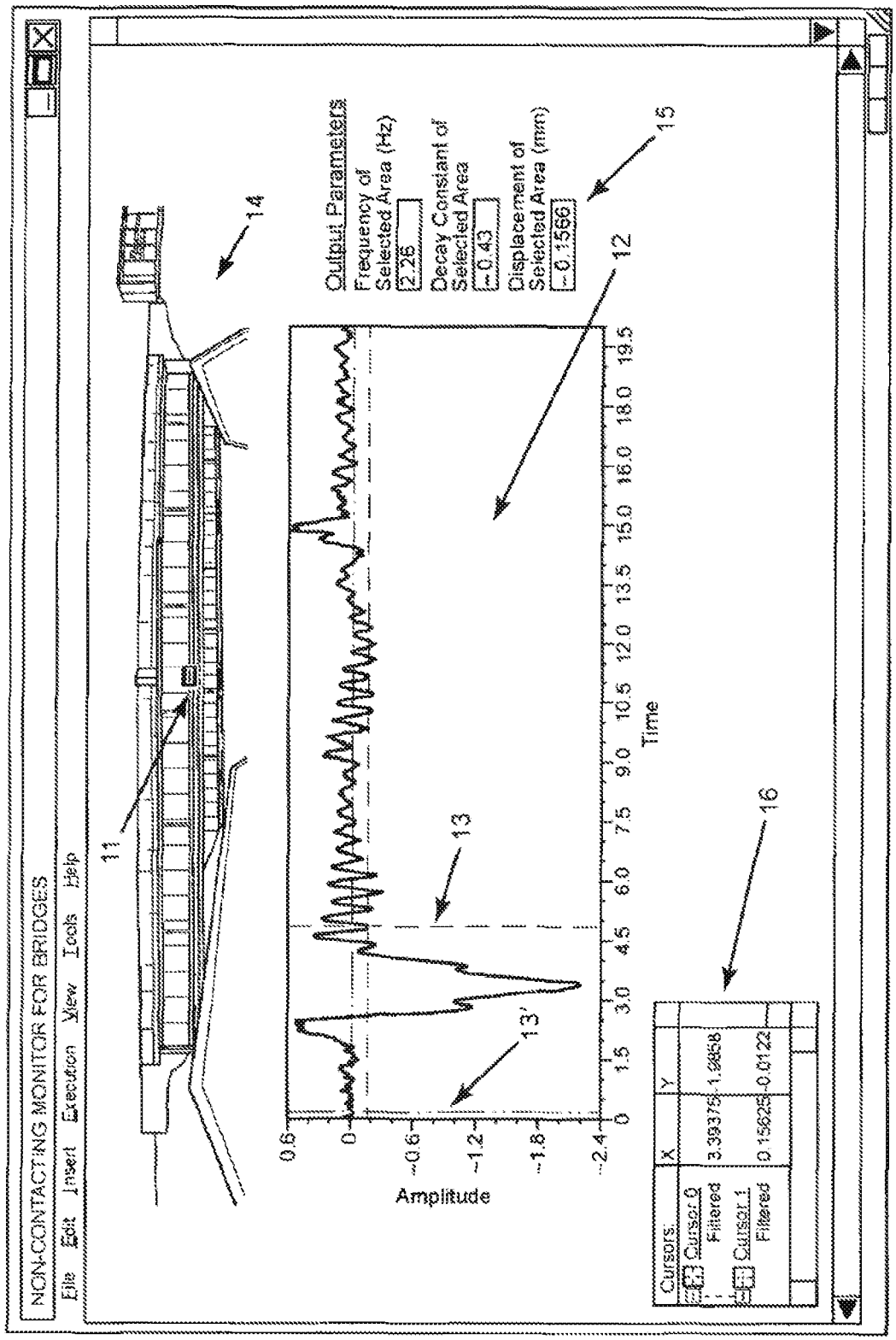
FIG. 3 is a schematic diagram of a GUI for the same video file as in the previous figure, but with a different instant time selected.

FIG. 3 shows a screen shot of the same analysis as in FIG. 2, but in this case the user has moved cursor 13 to a later time corresponding to a smaller displacement; in other words, the maximum load has passed and the structure is recovering and undergoing movement characteristic of damped oscillation. As can be seen from the new video frame 14', this time correlates with a moment when the large truck 3 has now moved some distance away from the selected area 11.

Example

Figure 4:
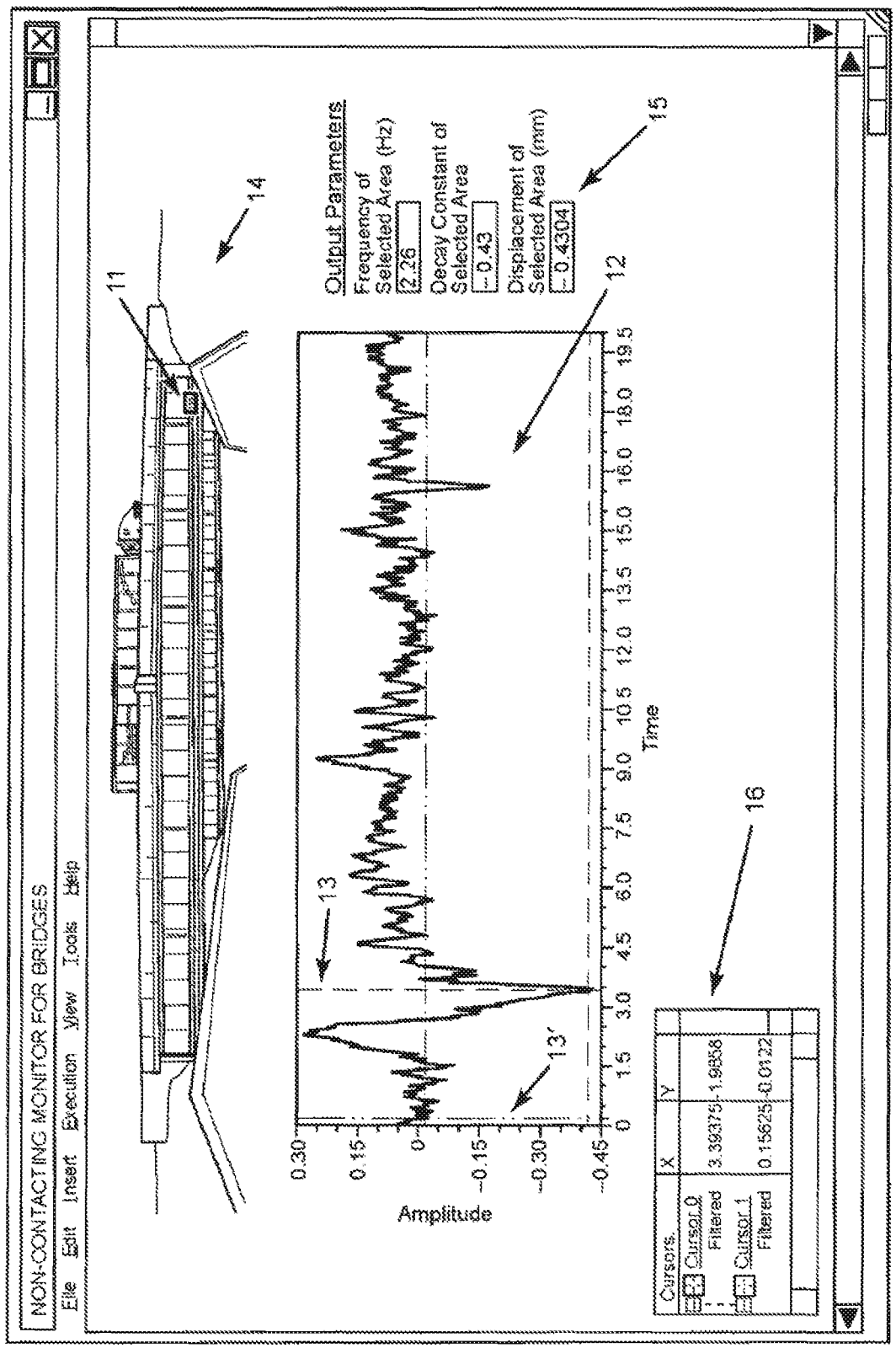
FIG. 4 is a schematic diagram of a GUI for the same video file as in the two previous figures, but with a different area of the structure selected.

FIG. 4 shows a screen shot of the same analysis as in FIG. 2, but in this case the user has moved the selected area 11 to a different position on the bridge, and has moved cursor 13 to the time corresponding to the maximum deflection. The new video frame 14" shows, as expected, that the truck 3 is again directly over the bridge. The maximum deflection of the new area 11 is significantly less than that of the first area (0.4 versus 2.1 mm), as expected because the new area is closer to the support whereas the first area was in the center of the span.

The GUI may be configured to choose an area for analysis in a number of different ways, which can be varied based on user convenience, the type of analysis being done, and the specific conditions of the site. For example, the user may draw a box of a selected size and shape, e.g., a square or rectangle. The rectangle may be longer in the direction normal to the expected motion in order to improve the signal-to-noise ratio. Alternatively, the movable indicator may consist of a crosshair or other graphic indicating an X-Y coordinate in the image; in that case, the user may select a size and shape of the area around the selected X-Y coordinate to be analyzed, and this area may be a single pixel (if the image contains a sufficiently well-defined edge) or a group of pixels, e.g., a square of 8×8 pixels centered on the crosshair. Lastly, the data processor may select the area(s) to be analyzed, as will be described in a later Example.

It will be appreciated that the GUI may optionally display various other calculated data, such as actual values of time and displacement corresponding to the graph and cursors in box 12. It may further display user-provided information such as time, date, location, bridge identifier (name, identification number, owner, etc.). Such information will typically be tagged as metadata corresponding to the video file. The video file and its metadata will preferably be archived in a database, to be used as described in several Examples to be discussed.

It will be understood that although screen shots of the GUI are rendered herein in black and white or grayscale, color rendering may be employed as well, particularly to enhance phase images or highlight certain effects where a color rendering is more readily apparent to the user than a grayscale rendering.

Example

It is important to note that the analysis method shown in the preceding Examples is conducted after the video file has been collected. This means that from a single video file, acquired in a matter of minutes from a safe position away from the bridge and traffic, the user can extract a huge amount of information that is both quantitative and easily compared to data taken at other places and times.

From one video file, the user can select many individual areas, one at a time, and see the displacement at each area for a single passing load (compare FIGS. 2 and 4). If there is a large difference between the deflections of these two points under the same load, this could indicate a local structural problem that requires attention.

By performing the same analysis on the same bridge at selected intervals (say quarterly, annually, etc.) the user can easily see if the structure (or a particular component of it) has degraded. By yielding quantitative data and archiving it over time, trends can be easily and unambiguously identified.

It will be appreciated that an inspector may calibrate the system to a fairly high degree in the case of bridges that are not heavily traveled, by employing a large vehicle of known weight to drive over the bridge while a video file is collected.

Comparing Similar Components for Analysis.

As shown in several examples above, the invention allows a user to start with a single video file and move successively from one point to another, and for each point, view the movement history of the selected point over the entire time span of the video. Various components of an object can therefore be measured and compared across the field of view. It will be appreciated that symmetries often exist within a structure that allow for motions of those features to be compared with each other. Absolute behaviors are not always necessary to know when doing comparisons. For example all elements of similar size and shape can be measured with respect to phase, displacement, and frequencies among other things. Then these components can be compared against one another for deviations in these properties. Likewise, sets of components can be measured and their differences can be compared to other sets.

A standard deviation of a certain property may be measured and all similar components' deviations compared against the standard deviation to look for outliers or components outside a set threshold.

An example may be a set of structural members that exist on a bridge in sets of two at intervals on both side of the bridge. The various behaviors of the sets may be compared against other sets, perhaps directly opposite on the bridge, or the average behavior of a set may be compared against the average behavior of other sets. These variations may be analyzed for outliers or deviations in behaviors.

These measurements may be used as a baseline either at initial measurement or on initial installation of a device or structure. Ongoing trending against this baseline may be used to find abnormal behavior. Behaviors after alteration or retrofits may be measured against these values to determine if the desired effect has taken place or if it has corrected outlier behavior.

Many structures, particularly bridges, exhibit bilateral symmetry. One may therefore expect similar characteristics on the left and right, or the front and back. It is highly unlikely that a defect or other fault occurs symmetrically. Therefore programmed logic may be effectively used to identify false positive findings if such findings are bilaterally symmetrical.

Linear progressive symmetries may also be used. Cables are tensile members clamped at either end. Between the two ends it is reasonable to assume a cable has a constant cross section, a constant modulus to density ratio, and constant tension. With this understanding it is reasonable to expect that nodes and anti-nodes will be regularly spaced and progressively responsive to given input energies.

Symmetries may therefore be used to identify similarities and differences. Unexpected observations may include cases that appear to be symmetrical when they should not be, and those which do not appear to be symmetrical when they should be. Either situation may be an indicator of a problem or a false reading, depending on the specific case. For a given structure or structure type, a knowledge base may be developed so that the system may interpret and double-check results automatically. Observations that are consistent with the prescribed knowledge base may be interpreted to be accurate findings, and observations that are contrary to the knowledge base may be flagged for further study.

Example

Applicants contemplate that each video file will preferably be archived, along with metadata identifying the structure and the structure type, along with the time, date, and other pertinent conditions, such as weather, traffic, etc. It will be appreciated that such a database would then allow the pooling of information and experience so that a particular user may compare the results to a more statistically robust population. The database administrator may provide various levels of access to various subscribers, and may, for example, allow a user to view performance data for comparable bridges while perhaps removing information that might identify the specific location or owner of another bridge in the database.

It will be understood that the term "database administrator" does not necessarily imply that a human administrator per se is involved in determining access. For example, particular access rules may be associated with particular types of subscriptions or licenses, and the system may grant various levels of access based on a subscriber's credentials. It will be further understood that access to a multi-user database would normally be controlled in both directions, i.e., requiring particular credentials for uploading new data into the database as well as for accessing existing (archived) data.

The database can allow a newly-built bridge to be tested and baselined before it is placed into service. If sufficient data exist for other bridges of the same type, a video file may be acquired using a truck of known weight and comparing the deflections with those of other bridges of similar design. If any deflections are unusually large compared to those of the "peer group", this could indicate that a construction defect exists, such as missing or loose bolts, missing or substandard welds, missing rebar, etc., and suggest that a hands-on inspection is needed before the bridge is approved or opened to traffic.

Example

The database may also be used by regulatory bodies, state-level Departments of Transportation, or others to quickly identify structures that need attention, need to have load limits reduced, or need to be inspected more frequently. In this way, limited resources may be used most effectively.

A well known problem arises when a caller reports that a possibly overweight vehicle was seen passing over a bridge. Although such a report might well be a "false alarm", it typically triggers a costly physical inspection to look for possible damage. If archived data exist for the bridge in question, a video inspection can be done and the displacements quickly compared to past results to determine if the structural integrity has been compromised. In a related situation, overweight vehicles are occasionally given a permit to cross a particular bridge. Comparing before-and-after video inspection files would document that the vehicle had not damaged the bridge.

Example

A bridge monitor and transmitter may be unmanned and recording continuously, buffering a certain amount of data and overwriting older data. In this case, a transient event caused by an overweight vehicle might trigger the archiving of a selected time span of the video record, along with automatic analysis and reporting via any suitable communication means, such as a cellular, WiFi, or hard wired connection.

The inventive system may use any number of methods to extract pertinent data from the video file, as described in the following Examples. It will be seen that in some cases, the specific analytical method may be set by the user via the GUI, or the analysis may to some extent be hidden as far as the user is concerned, or essentially a "black box", or prepackaged as a "recipe" to be followed. Some analysis procedures may be standardized and some internal decisions may be taken without user intervention. For example, if the system is intended to be used with a large number of substantially similar structures, a standard analysis procedure may be installed, so that each time a structure of a given type is analyzed, analogous areas are selected for study, or each time the system re-examines a particular structure the same areas are examined as were examined previously. Automating such decisions could reduce the level of variability and operator error and create a more consistent database.

In some cases, it is contemplated that the system may be permanently installed at a site and operate substantially autonomously over extended periods, with little or no user intervention.

Example

One suitable method for calculating displacements from video files is taught in U.S. Pat. No. 8,693,735, the entire disclosure of which is incorporated herein by reference. The displacement data shown in FIGS. 2-4 were calculated substantially according to this technique.

Example

For a bridge that may be heavily traveled or inspected frequently, a target or other fiducial mark may be permanently placed on one or more places on the structure to make displacement measurement easier and provide a reference point for future measurements.

Although in many Examples, it is contemplated that the video image is focused on a particular bridge or structural component under examination, from a vantage point on the ground, it will be appreciated that the invention may equally well be carried out in a reversed configuration in which the video camera is rigidly mounted on the bridge or component and is focused on a convenient stationary object in the environment. The fixed object might be a nearby landform, the edge of a building, bridge abutment, or other massive object. In such a configuration, the apparent motion of the fixed object will mimic the motion of the camera on the moving or vibrating component and the video file may be analyzed in a completely analogous manner as described earlier. It will be understood, in this case, that the motion of the camera might or might not be a perfect proxy for bridge motion, and in general it will not. Specifically, various displacement or vibration modes might exist in the camera mounting structure. If the camera is very rigidly mounted directly to a bridge beam, relative displacements between bridge and camera will be small and resonances will occur at very high frequencies. On the other hand, if the camera is mounted on a boom or a cantilevered arm as might be used in a street light or sign, then displacements relative to the bridge will inherently be higher and resonances will occur at lower frequencies. In some cases this may be usefully exploited; e.g., if it is known that vibrations at, say, 2 Hz would be damaging to the bridge, the camera mount might be intentionally configured to have a similar resonant frequency and thereby serve to visually amplify such movements and give an early warning that unsafe resonances are occurring.

Depending on the size and structural design of the bridge, it will in some cases be convenient to locate the camera on the bridge deck with a field of view encompassing overhead structural members, cables, and the like. In such situations, one may be able to view the structural member simultaneously with a portion of a building or other fixed object. The fixed object can then be used to correct for motions of the camera and thereby isolate motions of the structural member relative to the bridge deck.

Example

The invention may be temporarily deployed using a heavy, generally rigid base or tripod, and set up on a bridge with a clear line of sight to a stationary object such as a building. A vehicle of known weight (e.g., a 5-ton truck) would then drive across the bridge, and the apparent motion of the fixed object, calculated according to the inventive method, would serve as an accurate proxy for the real motion of the bridge. This configuration might be particularly suitable for situations in which it is difficult to find a good position on the ground from which to view the bridge (e.g., when dealing with a large span over a very wide waterway).

As described more fully in Applicant's co-pending application "Method of adaptive array comparison for the detection and characterization of periodic motion", one can determine the frequency and phase of vibrations induced in a structure by a dynamic load.

Example

Use of phase imaging is illustrated in FIG. 10.

Figure 10A:
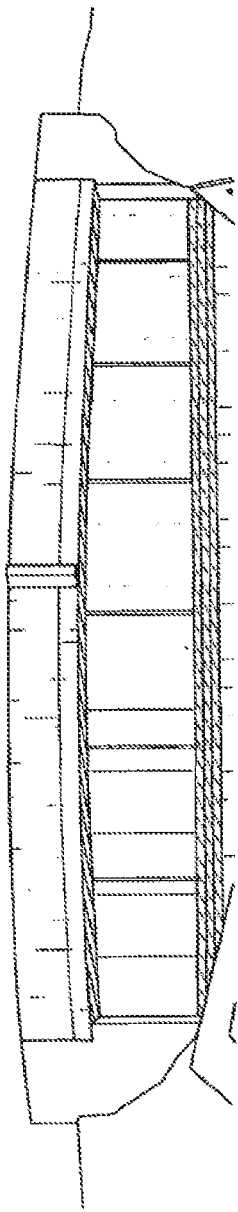
FIGS. 10A-10C illustrate the use of phase information to analyze vibrations in a bridge.

FIG. 10A shows a single image from a video sequence of a bridge. During this sequence a vehicle passed over the bridge (not shown).

Figure 10B:
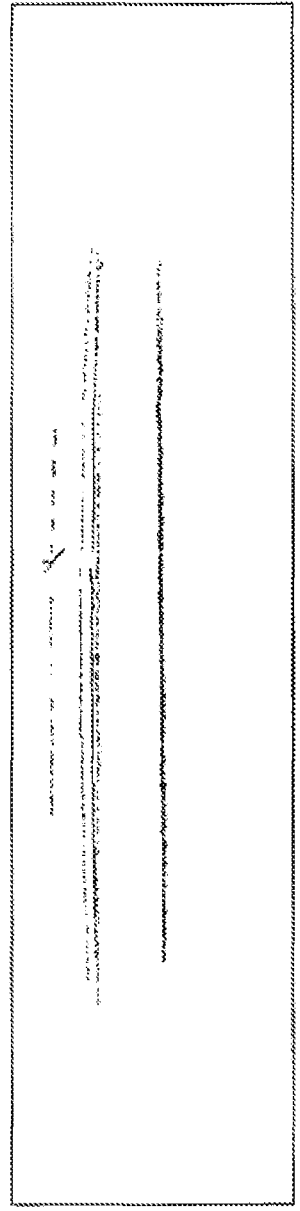

FIG. 10B shows a single phase mask image depicting a single phase (that of the fundamental vibration of the bridge) at 2.25 Hz, the bridge fundamental frequency. In this image things moving in phase show up as white (value 1) whereas things that are out of phase show as black (value 0). The image is scaled such that 0 is black and 1 is white. One can see that the motion on the I-beam support shows a clear feature of motion indicating the entire span is moving in phase with itself, as one would expect.

Figure 10C:
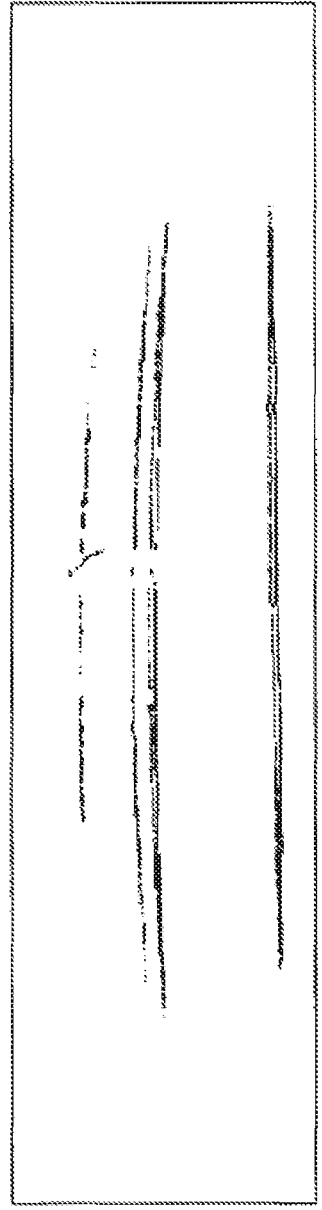

FIG. 10C shows an image of the phase mask seen in FIG. 10B multiplied by the intensity at each pixel of the amplitude of the 2.25 Hz signal, which relates to motion. One can see that now the phase image is scaled with relative values. Furthermore the image is much cleaner as small amplitudes of frequencies can be set below a threshold using the noise reduction technique.

Example

Another use of phase information is to examine localized areas to determine if two connections are vibrating in phase or out of phase with each other, which might have important diagnostic value in particular structures.

Use of associated audio data.

As noted earlier, many video recordings contain both image data and audio data collected and stored with a common time stamp. Applicants contemplate that the invention can exploit the associated audio data in a number of ways, with or without the use of a graphical user interface (GUI).

Example

The audio sensor (microphone) may be used to detect oncoming events and trigger the system to begin acquiring data (or analyzing data differently). A system positioned to monitor a bridge might, e.g., switch from a standby mode to an operating mode when the sound of an approaching train or truck is detected. This procedure might be particularly efficient in the case of railway bridges that are unloaded most of the time and are only loaded when a train is passing over.

Note that in this situation, the system might operate autonomously, with little or no human intervention during the triggering, acquisition, data analysis, and archiving processes.

Example

The system may include a GUI that takes advantage of time stamping so that the user may select a particular output feature (e.g., a maximum deflection in a bridge component) and the video frame corresponding to the time of that event will be displayed. If the complete video recording contains the audio track as well, the common time stamp will allow a segment of the audio to be played back for a time selected by the user for review. For example, if the user rewinds the file to review an off-normal event, the corresponding audio could be replayed to provide a better understanding of the nature and cause of the event.

To further increase the usefulness of the GUI as a visualization tool, images other than a raw video frame may be displayed instead of, or in addition to, the unprocessed video image, as described in the following Examples.

Example

The displayed video images may be modified and replayed in slow motion to visually amplify the apparent physical movement of a component or structure, as taught more fully in Applicant's co-pending application, "Method of adaptive array comparison for the detection and characterization of periodic motion." Such motion amplification can serve several purposes: First, it can give the user a better qualitative understanding of the motions of various structural elements. Second, it can serve as a visual guide to areas that might be most important to select with the movable indicator for detailed quantitative study.

For example, in a cable-supported bridge having many substantially similar cable supports, the amplified movement could immediately alert the user that one cable is loose, or for some reason moving substantially more than the others, even though the actual movement would be invisible to the naked eye.

Example

The display may include an Eigen image representing a sample plane (i.e., a single frequency) in the transformed X-Y-f space, to highlight the parts of the structure that are moving significantly at a particular frequency as taught generally by Kielkopf et al. in U.S. Pat. No. 8,693,735. The Eigen image may draw the user's attention to important structural issues, as the particular frequency may be associated with a particular defect, or movements at that frequency might be particularly damaging to the structure. Also, it will be understood that the natural frequency of a cable is directly related to the level of tension in the cable. Thus, if one cable has a substantially higher or lower resonant frequency than others (relative to its length), it might indicate that the particular cable is over- or under-tensioned and requires adjustment.

Example

The display may include a video frame that has been enhanced by summing the raw image with a difference image of the same view, with or without an amplifying factor applied, as taught in more detail in Applicant's co-pending application, "Method of adaptive array comparison for the detection and characterization of periodic motion."

Example

The GUI display may include an image frame enhanced to contain phase information, as taught in more detail in Applicant's co-pending application, "Method of adaptive array comparison for the detection and characterization of periodic motion." Such an image serves to highlight all the parts of the structure that are moving in phase with one another, providing further insights into the overall structural behavior.

Edge Detection and Enhancement

In some cases, it is useful to employ known methods to find and highlight edges. This may be done during setup of the camera at an inspection site, to allow an operator to be confident that the viewing location, lighting, weather, etc., are conducive to capturing useful video images. It may also be employed later on an archived video file to guide a user to well-defined edges where movements will be most easily characterized.

The invention may employ edge detection algorithms such as the Canny edge detector, which are familiar in the field of image processing. Such an edge detection method can be used in a variety of ways with respect to optical motion detection.

Example

Figure 12A:
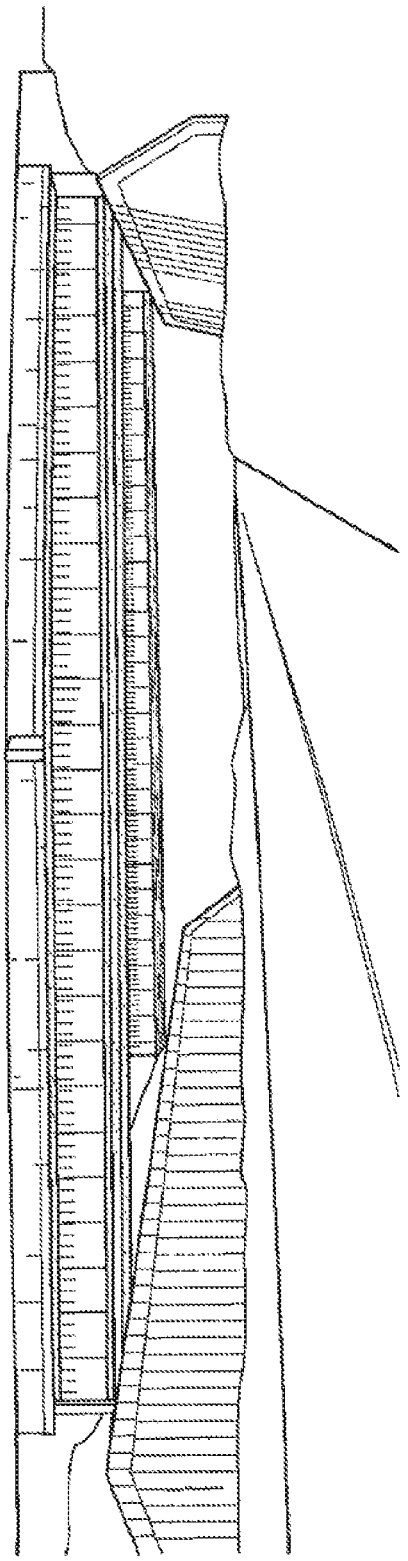
FIGS. 12A and 12B illustrate a video frame image containing an overlay generated by an edge detection process.
Figure 12B:
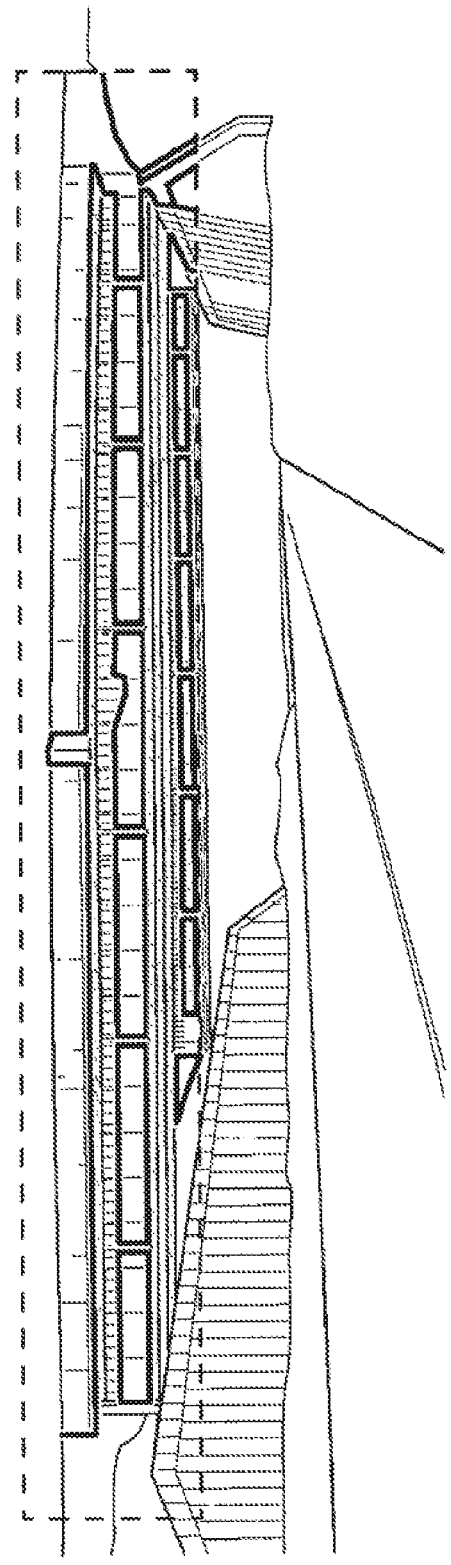

FIG. 12A shows an image of a bridge with edges highlighted using an edge detection algorithm. The analysis system could be programmed to use an edge overly such as shown in FIG. 12B and then crawl along those edges and measure displacement along the way. The output could be a plot of maximum displacement of each position on the bridge as a vehicle of known weight passed over In addition to a graphical displacement plot, the system may calculate the deflection at each point along the edge but then simply overlay the intensity of displacement onto the original image in, e.g., a color palette. This would produce an easily understood image similar to frequency images produced according to other aspects of the invention but calibrated to absolute displacement along the edges and displayed in either grayscale intensity or in a color palette.

Edges can be overlaid onto the imagery in video acquisition software in real-time. The edges can be set such that that various threshold levels determine what constitutes an edge, such as contrast and gradients. These edges can be used to determine if appropriate edges exist such that the user will have video data that is sufficient for optical motion detection of the edge. An automated program or user can ensure that certain locations within the image have edges that are of sufficient quality to ensure a proper measurement can be made. Likewise the same edge overlay can be used in post processing. The user can overlay edges or have a software program automatically overlay edges and use these edges to determine areas where good measurements can be made. The edge overlay can give the user a go/no-go situation in determining if a measurement can be made based on having the appropriate edge quality in the image.

The inventive system can use edge overlays in an autonomous fashion. The system can overlay edges in processing data and automatically determine where edge measurements can be made and then automatically proceed to make them, then report back the details of those results without human intervention.

The real-time edge overlay can be used to determine proper placement of the camera during acquisition. The edge overlay can also report back situations where conditions have occurred in which a proper measurement cannot be made.

A qualitative or quantitative interpretation by programmed logic such as a rules engine may then be used to accomplish one or more of the following tasks:
1. set a go/no-go flag for using a displacement, frequency, damping, or a phase finding in one portion at a particular time;
2. contribute a measure of confidence, positive or negative, to accompany findings associated with one portion at a particular time;
3. automatically report through an operator interface that a camera placement or field of view or settings are acceptable;
4. deduce a likelihood for a potential outcome is a false outcome (or not) such as a false positive or a false negative (or a true positive or a true negative);
5. deduce a vicinity in which a strongest pixel may be found;
6. deduce an association connecting multiple auto-selected pixels with a movement.

It will be appreciated that a user may, alternatively, draw a line using the GUI to define a particular edge to be followed, and then the system would automatically follow that line, calculate deflections or other values at each point along the line, and display the output as a graph, grayscale, or color rendering. This would be particularly useful to a user measuring the displacement of a long beam or girder.

Bridge Load Management and Enforcement

Many bridges have posted load limits, but in general compliance is largely voluntary on the part of the vehicle operator. Regardless of whether a load violation is willful or inadvertent, a vehicle that is greatly overweight may damage the bridge without anyone's knowledge. Such incidents are hard to detect and very difficult to enforce. Conversely, in certain circumstances, a vehicle may be given a permit to exceed the posted load limit on a particular bridge. Depending on the situation, it may be necessary to inspect the bridge before and after to insure that no damage was done by the permitted vehicle.

Example

Figure 5:
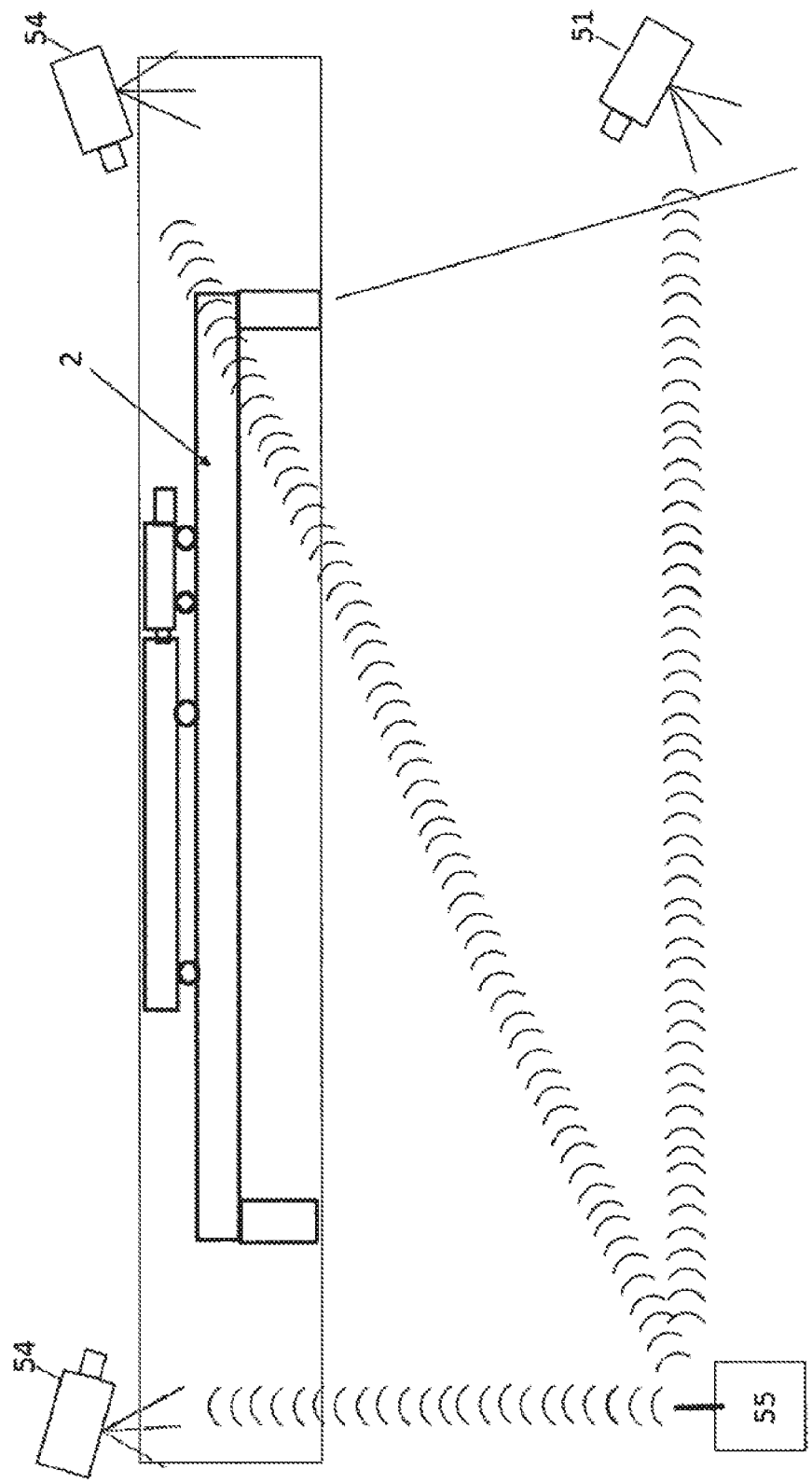
FIG. 5 is a schematic diagram of a system to monitor a bridge for load violations and load permitting.

FIG. 5 illustrates an example of a system configured to monitor and enforce load limits. An optical sensor 51 is fixedly mounted on a pole or other structure, at some convenient distance from bridge 2 and having an unobstructed view of at least a portion of the bridge. One or more cameras 54 are placed above the roadway and oriented to clearly view traffic on the bridge deck from both directions. Optical sensor 51 and cameras 54 communicate with a control system 55 that analyzes the output of optical sensor 51 to calculate the displacement of a preselected point on the bridge structure. When the calculated displacement exceeds a predetermined threshold (indicating an overload condition) an event is triggered and time-stamped, and cameras 54 are triggered to capture images of the vehicle(s) on the bridge, and those images are time-stamped and archived along with time-stamped displacement data.

Optical sensor 51 may be a simple optical detector or a video camera, as taught in the aforementioned U.S. Pat. No. 8,693,735, and using the analysis methodology taught therein. Alternatively, the displacement analysis may be done by any suitable means as described above. It will be understood that the cameras 54 on the bridge may communicate with controller 55 using cables or via a wireless connection using any suitable protocol compatible with the need to time stamp the data.

The documentation produced by this system may be used in various ways: 1. An officer may review the data and vehicle images and, if appropriate, issue a citation to the owner of the offending vehicle. 2. Subsequent data may be reviewed to determine if the bridge was damaged by the incident. 3. The images may reveal that the vehicle was permitted to be overweight on that occasion and no action is needed. 4. The images may show that no one vehicle led to the overload, but that traffic patterns overall have changed, and greater traffic loading on that bridge may require that the bridge needs improvements to meet the increased structural demand.

Cable Bridge Analysis

Example

A cable bridge may be conveniently analyzed by first collecting a video file of the entire bridge or a substantial portion of it. The area selector is then configured in the form of a rectangle enclosing a single cable. Analysis of this cable may include displacement, resonant frequency, phase images, etc. Moving sequentially from one cable to the next, and comparing each to the others, one might observe differences and surmise that a particular cable may be under more or less tension than it should be, or that there are problems with the end connections, etc., indicating that a physical inspection is called for.

It will be appreciated that for the case of a relatively complex bridge that will be inspected regularly, many of the foregoing steps may be automated, so the user starts with the raw video file and runs a recipe specific to that bridge.

The inventive system may also be deployed permanently and operate with a high degree of autonomy, as described in the following Example:

Example

For autonomous operation, the camera would be installed permanently or semi-permanently in a weatherproof enclosure positioned to view the selected structure. It would begin with a learning mode in which it measures various parts of the bridge over time (e.g., one month). The system would use these calculations to establish a baseline, and then transmit data at selected intervals going forward. The system may further report any values that deviate from the baseline values by a predetermined amount. A single instance of values above a threshold might indicate that an overweight vehicle had passed, whereas a trend of higher values would indicate potential structural degradation. The system may be programmed to make such distinctions according to a predetermined set of rules.

It will be understood that in this Example, all or some of the actual calculations may be done locally, whereas other calculations (e.g., comparison with other bridges in a central database) may be done by a remote system hosting a database or generating a report.

Seismic Testing and Modeling

The preceding Examples describe the use of the invention on actual civil infrastructure, such as a bridge, overpass, or the like. It will be appreciated that the inventive concept is equally applicable to the analysis of structural scale models, particularly those used in seismic testing. Generally speaking, the static analysis of even fairly complex structures such as tall buildings is tractable by either standard methods or by finite-element techniques. It is recognized, however, that first-principles analysis of the harmonic response of a complex structure under dynamic loading can become intractable, particularly when it involves the complex motions associated with seismic events. For this reason, scale models are built and tested in a seismic simulator. The simulator has a large flat surface that can be driven in three dimensions by a series of actuators to replicate, in scale, the ground movement associated with a particular seismic event, which may be theoretical or reconstructed from historical seismic data from past earthquakes. Typical of the art are simulators made by MTS Systems Corp., Eden Prairie, Minn., and by Servotest Testing Systems Ltd, Surrey, England.

Example

Figure 6:
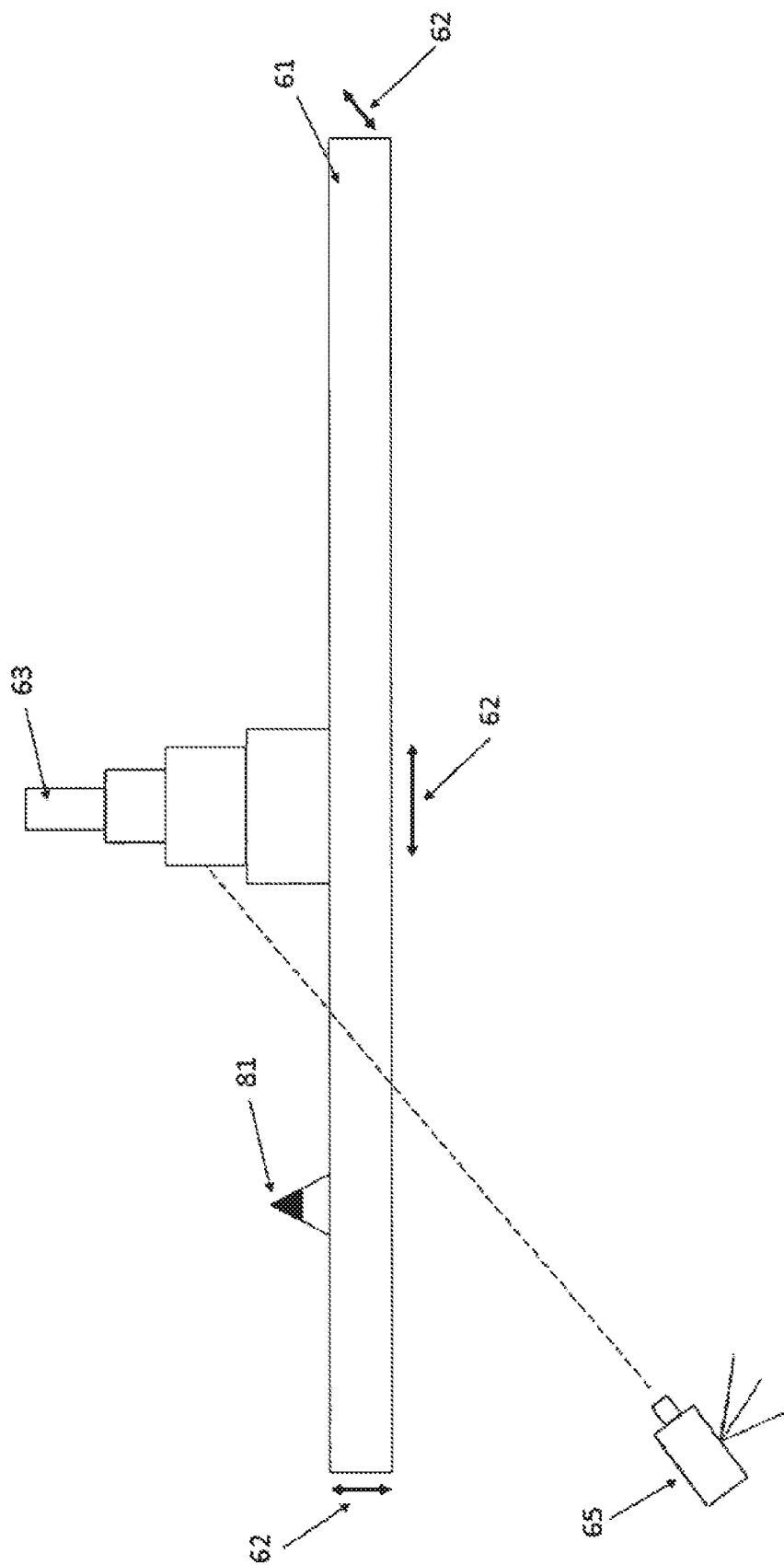
FIG. 6 is a schematic diagram of a system for observing model deflections during seismic testing.

FIG. 6 shows an example of the use of the invention in conjunction with a seismic simulator. Platform 61 is driven by actuators (not shown), which allow the platform to be moved at selected amplitudes and frequencies in three dimensions. A structural model 63 is secured on the platform. A controller (92 in FIG. 9) provides signals to the actuators (93 in FIG. 9) in order to generate, in scale, the selected earth movements 62 to be simulated in three directions as shown. Video camera 65 collects video files while the platform 61 is moving, for later analysis. Analysis of these files may be done using the GUI and methods generally described above. Some modifications may preferably be made to adapt the invention to the specific case of seismic analysis.

It will be appreciated that in the forgoing Examples using real structures, the ground under the structure is assumed to be stationary. However, in the seismic simulator, the entire structure is sitting in a moving frame of reference. It may be desirable to normalize the observed motions of any particular point on the model to their true values relative to the frame of reference. There are several ways to do this.

Figure 7:
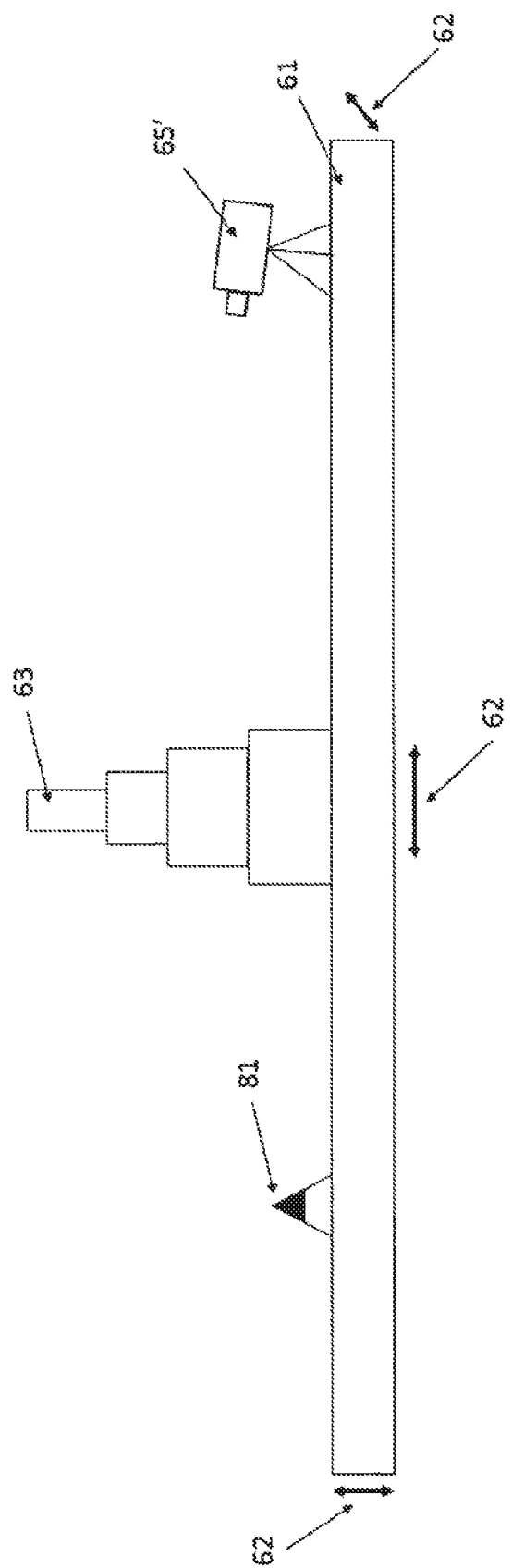
FIG. 7 is a schematic diagram of another system for observing model deflections during seismic testing.

If the video camera 65' is sufficiently vibration resistant, it can be securely attached to the moving platform 61 as shown schematically in FIG. 7 and will therefore automatically view the true motions of the model relative to the common frame of reference.

Figure 8:
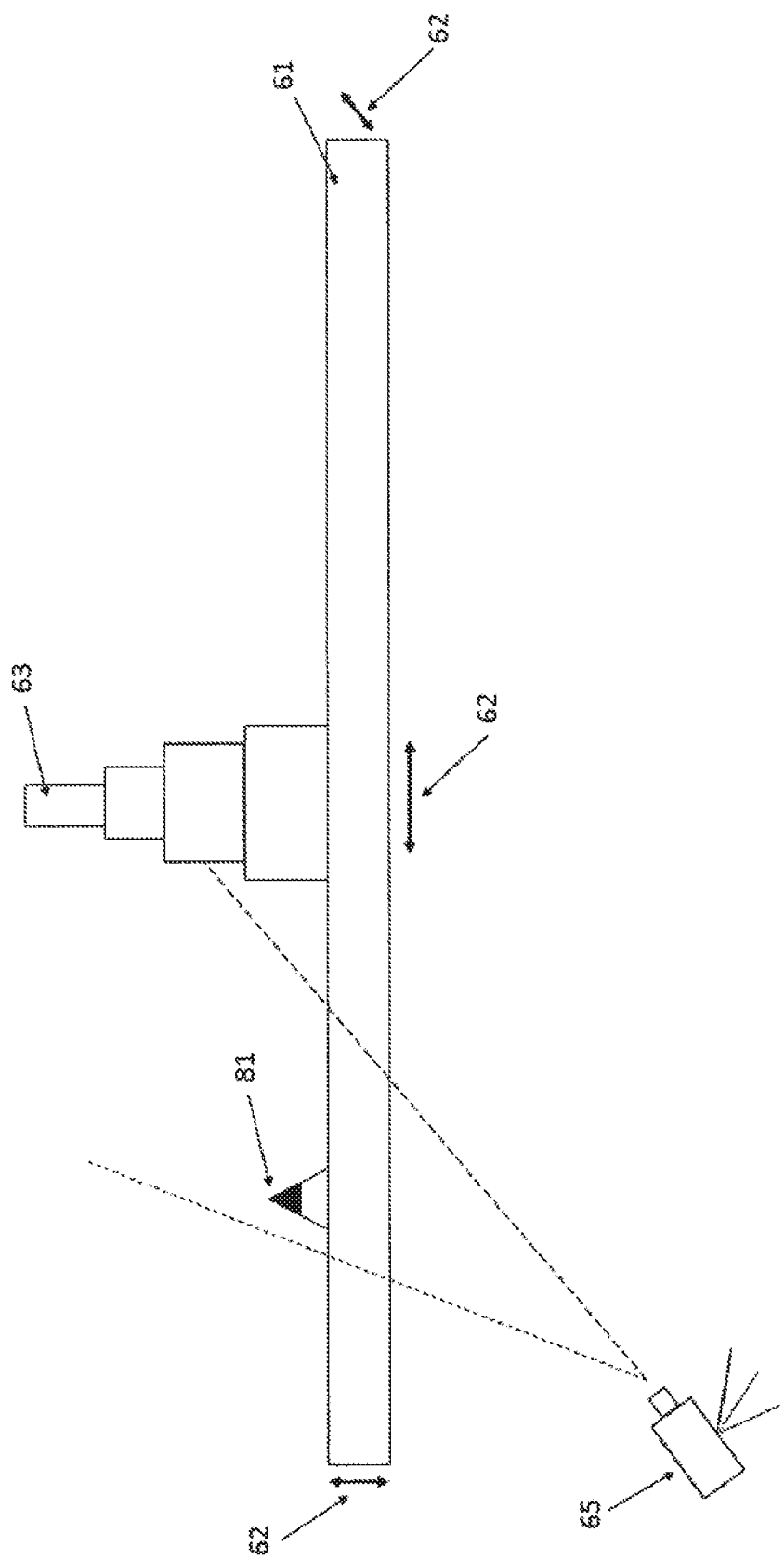
FIG. 8 is a schematic diagram of another system for observing model deflections during seismic testing.

A reference object 81 that is very rigid (a small solid block or pyramid) may be affixed to the moving platform 61 and the camera 65 oriented to view both the reference object and the model, as shown schematically in FIG. 8 so that relative movements of the model relative to the reference object may be calculated.

An interface 91 may be provided to synchronize the video camera 65 with the X-Y- and Z-axis control signals from controller 92 driving the actuators 93, as shown schematically in FIG. 9. This may be done in real time, or the interface may provide a time stamp at one or more times during the test so that the video data can later be matched or synchronized with the calculated position of the frame of reference.

In all of the configurations in FIGS. 6-9, it will be understood that several cameras may be used and synchronized to provide views of model 63 from several directions simultaneously. So, for example in the configuration shown schematically in FIG. 7, one camera may be positioned at the center of one edge of table 61, essentially viewing along the x-axis of vibration 62, and a second camera may be positioned at the center of an orthogonal edge of table 61 and viewing along the y-axis of vibration 62. The z-axis of movement (vertically or normal to the surface of table 61) will be viewed by both cameras, thereby capturing the complete record of movements in all three spatial dimensions.

A simple demonstration of the application of the invention to seismic testing was done using a video taken by a third party completely without the inventive process in mind, as described in the following Example.

A short instructional video was posted on the internet, showing operation of a benchtop seismic simulator [Model K50-1206, NaRiKa Corp., Tokyo, Japan]. A small model of a simple seven-floor structure contained a hanging ball in the center of each story to better visualize the motions and resonances that arise in response to various earth movements. Technical details of the video clip are as follows:
Video ID: y6Z9bsGkMsc
Dimensions: 640×480*1.75
  Stream type: https
A segment of this video devoted to the building model, comprising 454 frames representing about 20 seconds of running time, was analyzed using the invention. Working from this one video file, one can select any location and determine the frequency spectrum and the displacement vs. time, and plot these variables using the graphical user interface. Eigen images for particular frequencies may be displayed for visual comparison to the raw video in order to see which parts of the structure have a large vibrational component at that frequency.

Figure 11A:
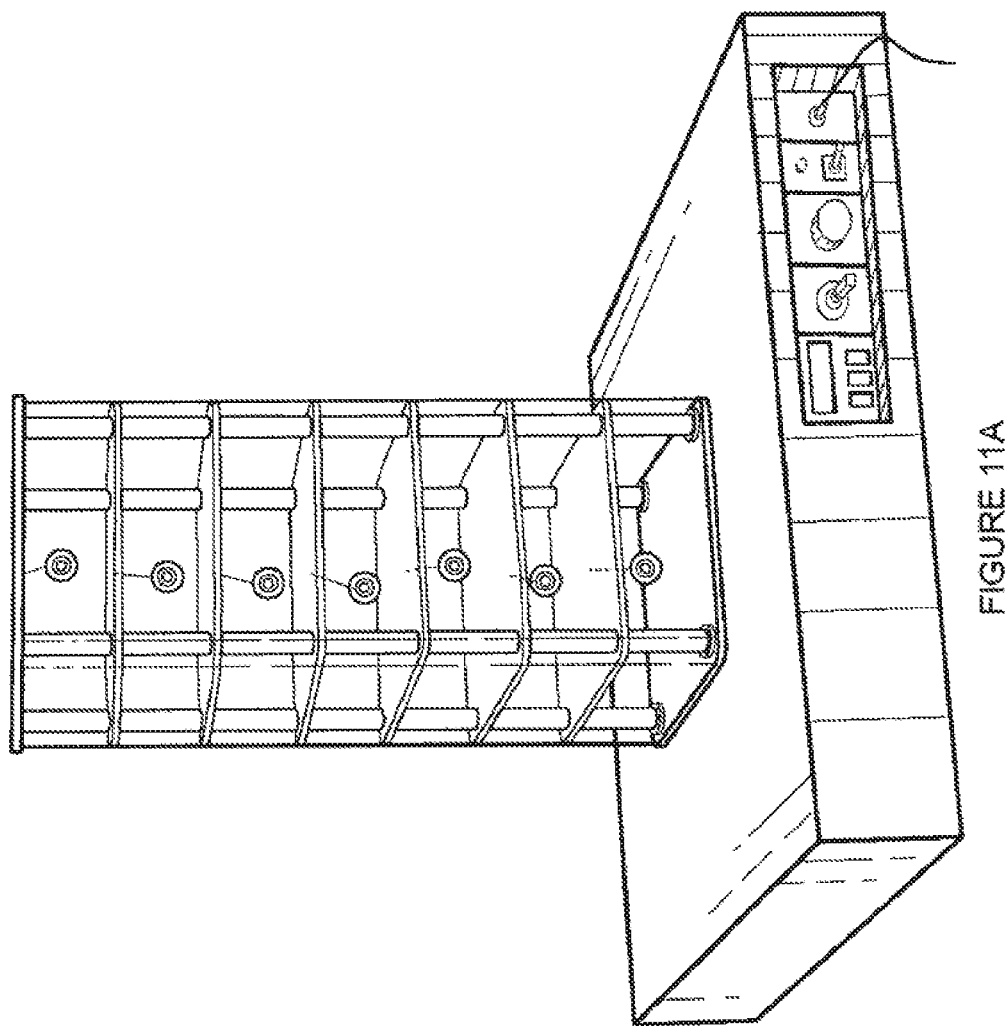

Exemplary results are shown in FIG. 11. FIG. 11A is one frame of the raw video, showing a model under test. FIG. 11B shows the image representing 4.63 Hz, and FIG. 11C shows the image representing 2.84 Hz. Note that faint markings at the bottom of FIGS. 11B and 11C are artifacts that arose because the original raw video contained a superimposed title graphic; these artifacts do not detract from the analysis of the Eigen images (FIGS. 11B and 11C), which can quite clearly be correlated to the moving structural elements in the raw video from (FIG. 11A).

At the same time, the user can look at the platform itself (or a fiducial object fixed thereon) to see driving frequencies, the orbit (x and y components) of the platform, and the amplitudes of displacement of the platform. This is simultaneous with the information gathered on the structure, and provides valuable insights connecting structural vibrations to the ground movements that are driving them.

What is claimed is:

1. A system for monitoring the motion of a first object having at least one surface that reflects light from an environment surrounding the first object and having the capacity to store heat from said environment, comprising:
  a video camera which can be stably positioned at a selected distance from the first object with an unobstructed view of at least a portion of the first object, wherein the video camera acquires images of the first object which are able to be divided into a plurality of pixels, wherein the pixels are characterized by an intensity associated with one or both of visible light energy from light reflected from the at least one surface of the first object or infra-red energy emitted from thermal heating of the at least one surface of the first object over a selected time interval, and wherein the images are arranged in a plurality of frames; and
  a data processing system configured to obtain a first measurement of an intensity of a first location of at least one frame comprising at least one pixel and a second measurement of an intensity of a second location of the frame comprising at least one pixel apart from the first location, determine a difference in the first measurement and the second measurement, and display at least one image from the frame,
  wherein the data processing system is further configured to modify the displayed image to indicate a difference in a phase of motion between the first object and at least a second object based on the difference in the first measurement and the second measurement.

2. The system of claim 1, wherein the object in the displayed image is a first object, and a phase indication of the first object is binary such that a second object in the displayed image is represented to be either within a predetermined phase range with the first object or outside of the predetermined phase range.

3. The system of claim 2, wherein the data processing system is further configured to apply a color scheme to represent the second object as being within the predetermined phase range or outside the predetermined phase range.

4. The system of claim 3, wherein the phase indication is shown only for a location of pixels associated with an object within the predetermined phase range.

5. The system of claim 1, wherein the data processing system is further configured to apply a color scheme to represent a phase angle of the object in the displayed image.

6. A system for monitoring the condition of a structure, the structure having at least one surface that reflects light from an environment surrounding the structure and having the capacity to store heat from said environment, comprising:
- a video camera which can be stably positioned at a selected distance from the structure with an unobstructed view of a selected portion of the structure, wherein the video camera acquires images of the structure which are divisible into a plurality of pixels, wherein the images are arranged in a plurality of frames comprising at least a first frame and a second frame; and,
- a data processing system configured to monitor a change in a measurement of intensity of at least one pixel in the first frame compared to the second frame, wherein the intensity results from one or both of visible light energy resulting from light reflected from the at least one surface of the structure or infra-red energy emitted from thermal heating of the structure over a selected time interval, and to calculate a physical parameter related to movement of said selected portion of said structure as a function of time, and compares the calculated physical parameter to baseline limits to identify at least one condition related to the structure.

7. The system of claim 6, wherein said structure is selected from the group consisting of buildings, models of buildings, beams, cables, actuators, mechanical support structures, towers, rotating equipment, reciprocating equipment, piping, ducts, conveyors, and presses.

8. The system of claim 6, wherein said physical parameter related to movement of said selected portion of said structure is selected from the group consisting of: physical displacement; frequency; phase; maximum displacement; and damping rate.

9. The system of claim 6, wherein said baseline limits are established by using a test vehicle of known weight or a test apparatus delivering a known force to the structure under test.

10. The system of claim 6, wherein said baseline limits are established by corresponding measurements from a population of other structures of known and similar design.

11. The system of claim 6, wherein said baseline limits are established by corresponding measurements from one or more similar elements on the structure and at least one change in a dynamic property of the structure is determined by changes in symmetry of measurements for the similar elements.

12. The system of claim 6, wherein said measured parameter is made at multiple locations on the structure identified by the user using a GUI that locates regions of interest on the structure.

13. The system of claim 6, wherein said measured parameter is made at multiple locations on the structure identified by the user using one or more fiducial marks mounted on the structure.

14. The system of claim 6, wherein the data processing system is further configured to calibrate a camera position with respect to the structure, wherein said camera position is maintained, checked, or corrected by using one or more fiducial marks permanently mounted on the structure.

15. The system of claim 6, wherein the data processing system is configured to trigger an alert, generate a time stamp, and save the recorded data to permanent storage when the measured physical parameter exceeds a preset threshold indicating an overload condition.

16. The system of claim 15, further comprising a second video camera which can be mounted to view the structure from a different perspective than the first video camera, wherein the second video camera is triggered by the alert to acquire and save a recording which can be used to identify the vehicle or other external conditions initiating the overload condition.

17. The system of claim 6, wherein the data processing system is triggered by an external alert from an audio sensor used to detect oncoming events, whereby the system generates a time stamp, and saves the recorded data to permanent storage along with any metadata which provides supporting documentation related to the event.

18. A system for monitoring the model of a structure, the model having at least one surface that reflects light from an environment surrounding the model and having the capacity to store heat from said environment, comprising:
- a video camera which can be stably positioned at a selected distance from the model with an unobstructed view of a selected portion of the model, wherein the video camera acquires images of the model which are divisible into a plurality of pixels, wherein the images are arranged in a plurality of frames comprising at least a first frame and a second frame; and,
- a data processing system configured to monitor a change in a measurement of intensity of at least one pixel in the first frame compared to the second frame, wherein the intensity results from one or both of visible light energy resulting from light reflected from the at least one surface of the model or infra-red energy emitted from thermal heating of the model over a selected time interval and calculate a physical parameter related to movement of said selected portion of said model as a function of time, which result from applying a regime of test conditions.

19. The system of claim 18, wherein a subject of said model is selected from the group consisting of buildings, beams, cables, actuators, mechanical support structures, towers, rotating equipment, reciprocating equipment, piping, ducts, conveyors, and presses.

20. The system of claim 19, wherein said physical parameter is selected from the group consisting of: physical displacement; frequency; phase; maximum displacement; cable tension; and
damping rate.

21. A system for monitoring the condition of a structure which is supported by supporting cables, the structure having at least one surface that reflects light from an environment surrounding the structure and having the capacity to store heat from said environment, comprising:
- a video camera which can be stably positioned at a selected distance from the structure with an unobstructed view of a selected portion of the structure, wherein the video camera acquires images of the structure which are divisible into a plurality of pixels, wherein the images are arranged in a plurality of frames comprising at least a first frame and a second frame; and,
- a data processing system configured to monitor a change in a measurement of intensity of at least one pixel in the first frame compared to the second frame, wherein the intensity results from one or both of visible light energy resulting from light reflected from the at least one surface of the structure or infra-red energy emitted from thermal heating of the structure over a selected time interval and calculate a physical parameter related to movement of one or more cables supporting said structure as a function of time, and determines if the calculated physical parameter falls within expected limits or outside a predetermined threshold associated with at least one of the supporting cables.

22. The system of claim 21, wherein said physical parameter related to movement of said cables supporting said structure is selected from the group consisting of: physical displacement; frequency; phase; maximum displacement; cable tension; and damping rate.

\* \* \* \* \*